United States Patent
Pisharodi

(10) Patent No.: US 11,052,169 B1
(45) Date of Patent: Jul. 6, 2021

(54) SYSTEMS, APPARATUS AND METHODS FOR PURIFYING AIR

(71) Applicant: Madhavan Pisharodi, Brownsville, TX (US)

(72) Inventor: Madhavan Pisharodi, Brownsville, TX (US)

(73) Assignee: Perumala Holdings, LLC, Brownsville, TX (US)

( * ) Notice: Subject to any disclaimer, the term of this patent is extended or adjusted under 35 U.S.C. 154(b) by 0 days.

(21) Appl. No.: 16/987,011

(22) Filed: Aug. 6, 2020

Related U.S. Application Data

(60) Provisional application No. 63/022,307, filed on May 8, 2020, provisional application No. 63/029,290, filed on May 22, 2020.

(51) Int. Cl.
| | |
|---|---|
| *A61L 9/20* | (2006.01) |
| *F24F 3/16* | (2021.01) |
| *F24D 15/00* | (2006.01) |
| *B01D 46/10* | (2006.01) |
| *B01D 46/00* | (2006.01) |
| *A62B 11/00* | (2006.01) |

(Continued)

(52) U.S. Cl.
CPC ........ *A61L 9/20* (2013.01); *A62B 7/02* (2013.01); *A62B 9/00* (2013.01); *A62B 11/00* (2013.01); *A62B 23/00* (2013.01); *B01D 46/0028* (2013.01); *B01D 46/0049* (2013.01); *B01D 46/10* (2013.01); *B64D 13/08* (2013.01); *B64F 5/30* (2017.01); *F24D 15/00* (2013.01); *F24F 3/16* (2013.01); *A61L 2209/12* (2013.01); *A61L 2209/14* (2013.01); *A61L 2209/16* (2013.01); *B01D 2273/26* (2013.01); *B01D 2273/30* (2013.01); *B01D 2279/50* (2013.01); *B01D 2279/65* (2013.01); *B64D 2013/0651* (2013.01); *B64D 2013/0688* (2013.01); *F24F 8/22* (2021.01)

(58) Field of Classification Search
None
See application file for complete search history.

(56) References Cited

U.S. PATENT DOCUMENTS

| | | | |
|---|---|---|---|
| 4,798,702 A | * | 1/1989 | Tucker ............... A61L 2/10 210/748.11 |
| 5,656,242 A | | 8/1997 | Morrow et al. |

(Continued)

OTHER PUBLICATIONS

'How a packaged system works' (Goodman) Jul. 29, 2016, [online] retrieved from <URL: https://web.archive.org/web/20160729193422/https://www.goodmanmfg.com/resources/heating-cooling-101/how-a-packaged-system-works>.

*Primary Examiner* — Holly Kipouros
(74) *Attorney, Agent, or Firm* — D'Ambrosio & Menon, PLLC; Usha Menon

(57) ABSTRACT

Systems, apparatus and methods for disinfection of airflow. An apparatus for disinfecting air-conditioned airflow in a confined space includes: a modular housing; and a disinfection chamber enclosed within the housing. The disinfection chamber includes a plurality of disinfection sheets. Each disinfection sheet comprises a plurality of ultraviolet (UV) light sources. The airflow is configured to be routed along a serpentine pathway within the housing to expose microorganisms in the airflow to far UV-C light emitted by the UV light sources for an extended and optimal duration.

12 Claims, 25 Drawing Sheets

(51) Int. Cl.
  *A62B 23/00* (2006.01)
  *A62B 7/02* (2006.01)
  *A62B 9/00* (2006.01)
  *B64D 13/08* (2006.01)
  *B64F 5/30* (2017.01)
  *B64D 13/06* (2006.01)
  *F24F 8/22* (2021.01)

(56) References Cited

U.S. PATENT DOCUMENTS

| | | |
|---|---|---|
| 7,185,510 B2 | 3/2007 | Lee et al. |
| 8,336,821 B2 | 12/2012 | Shell et al. |
| 2002/0162968 A1* | 11/2002 | Snowball ................ C02F 1/325 250/432 R |
| 2006/0057020 A1 | 3/2006 | Tufo |
| 2008/0173178 A1 | 7/2008 | Metteer |
| 2012/0248332 A1* | 10/2012 | Kreitenberg ........... A63B 47/04 250/455.11 |
| 2015/0209457 A1* | 7/2015 | Bonutti .................. C02F 1/325 250/435 |
| 2016/0001108 A1 | 1/2016 | Zhou et al. |
| 2018/0250430 A1 | 9/2018 | Machovina et al. |
| 2020/0282086 A1* | 9/2020 | Silverman ............ A61L 2/0047 |

* cited by examiner

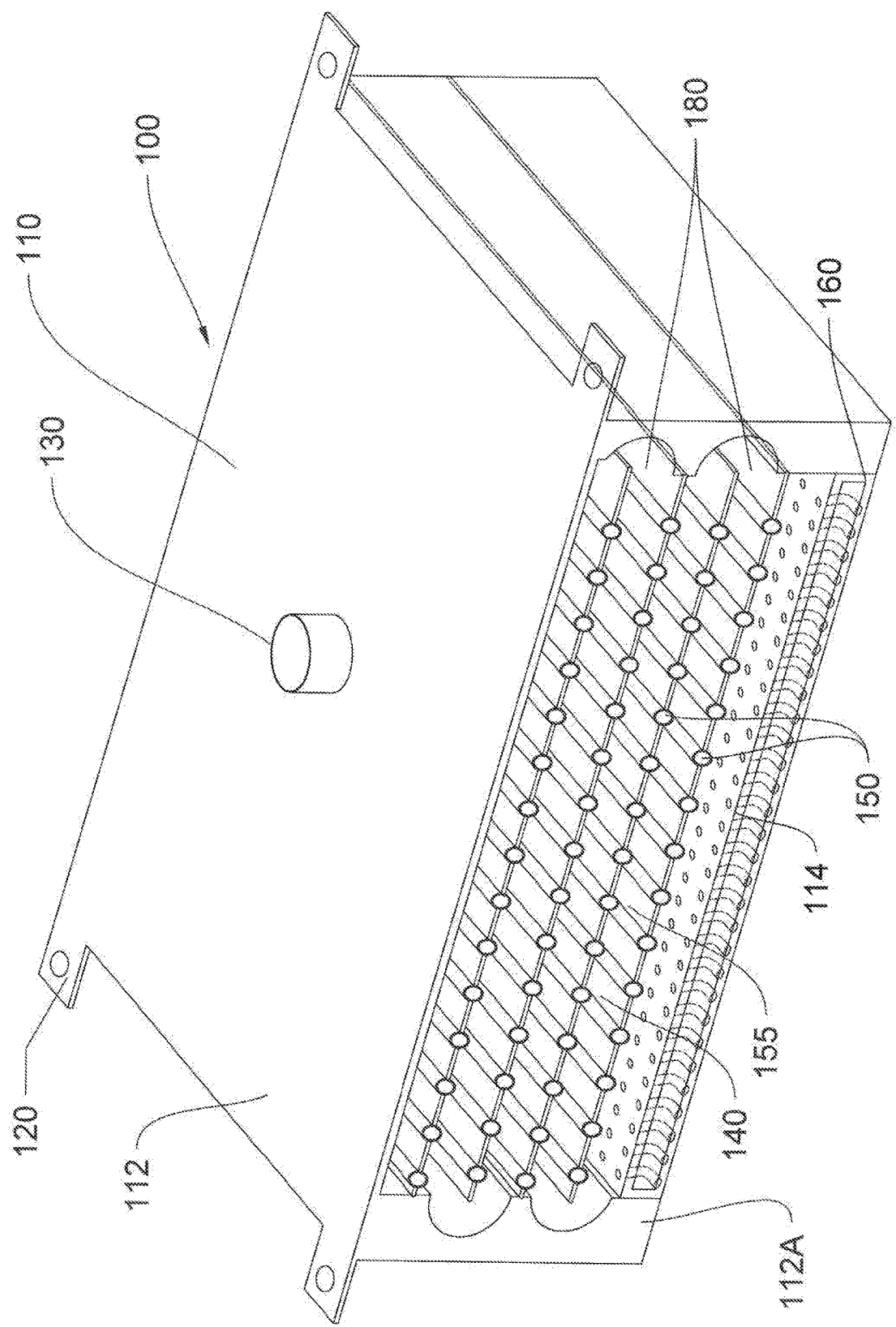

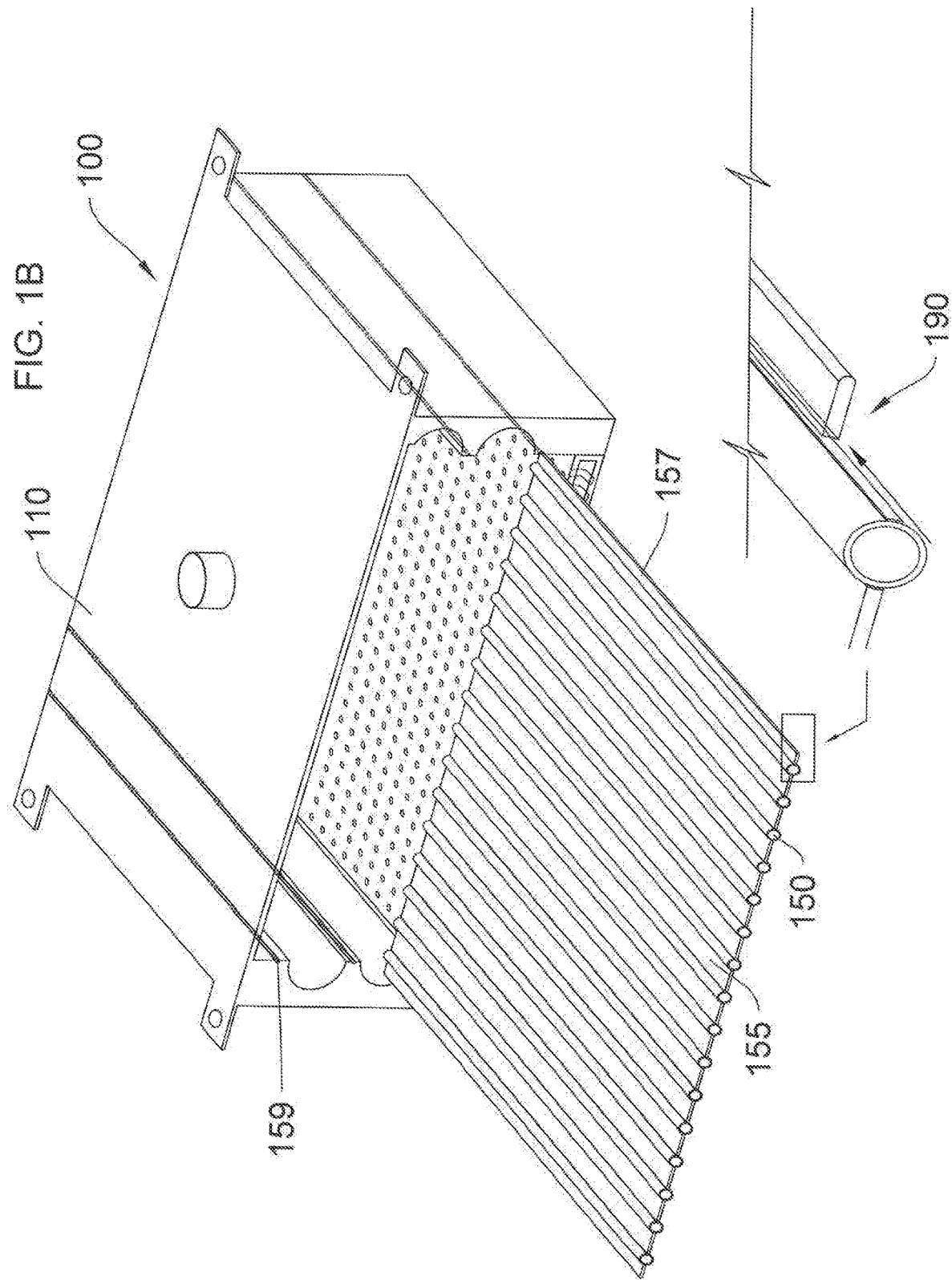

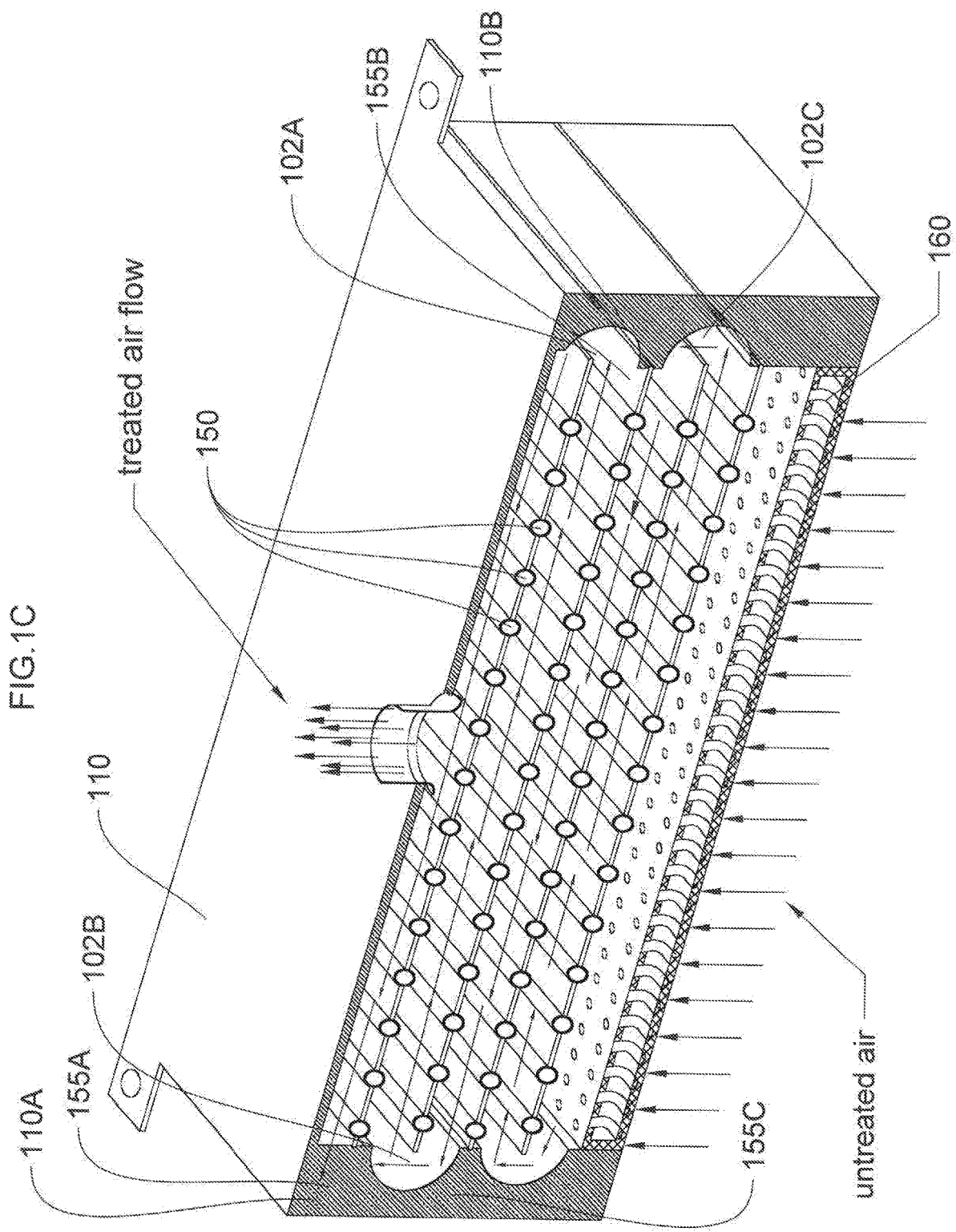

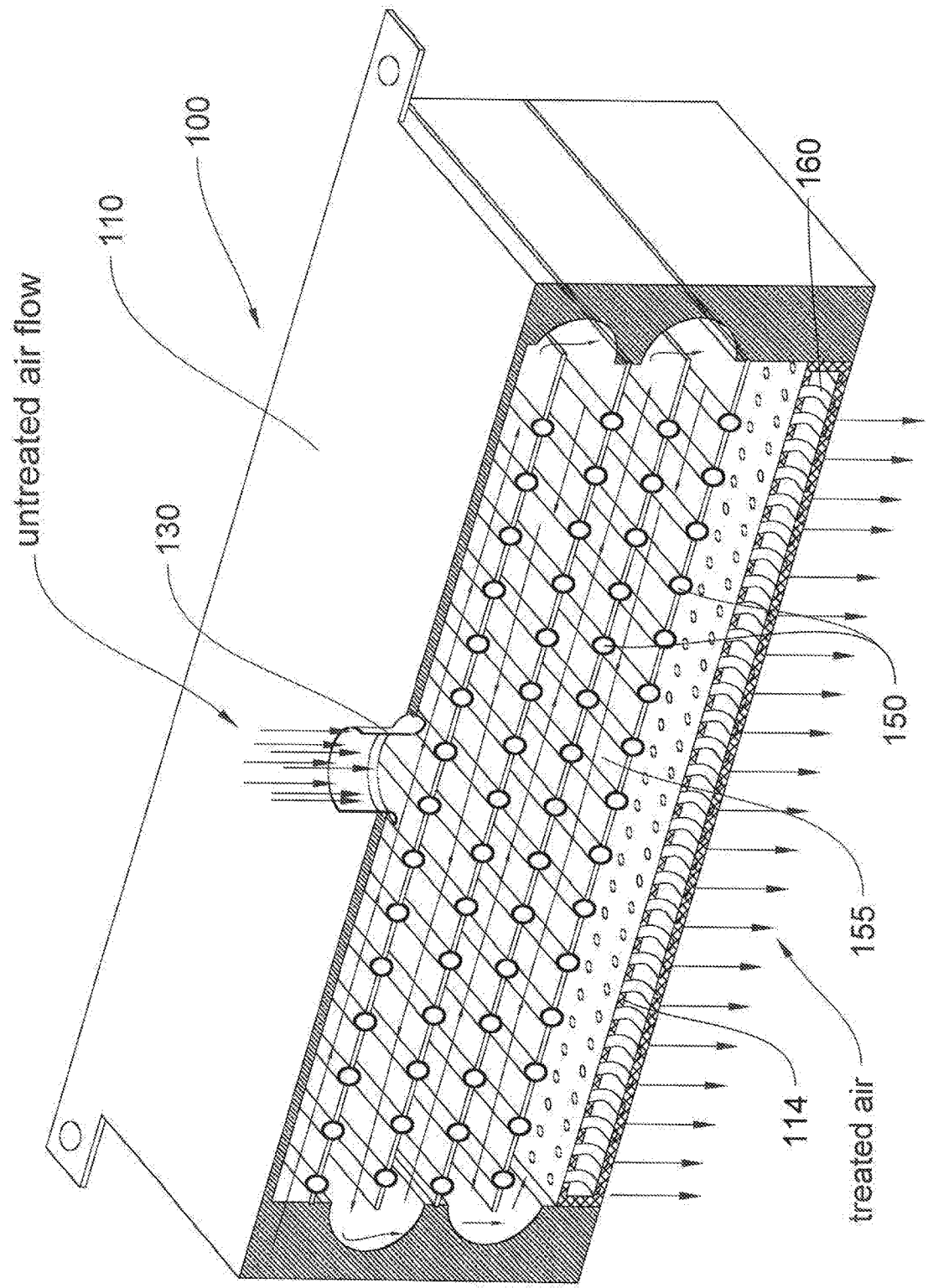

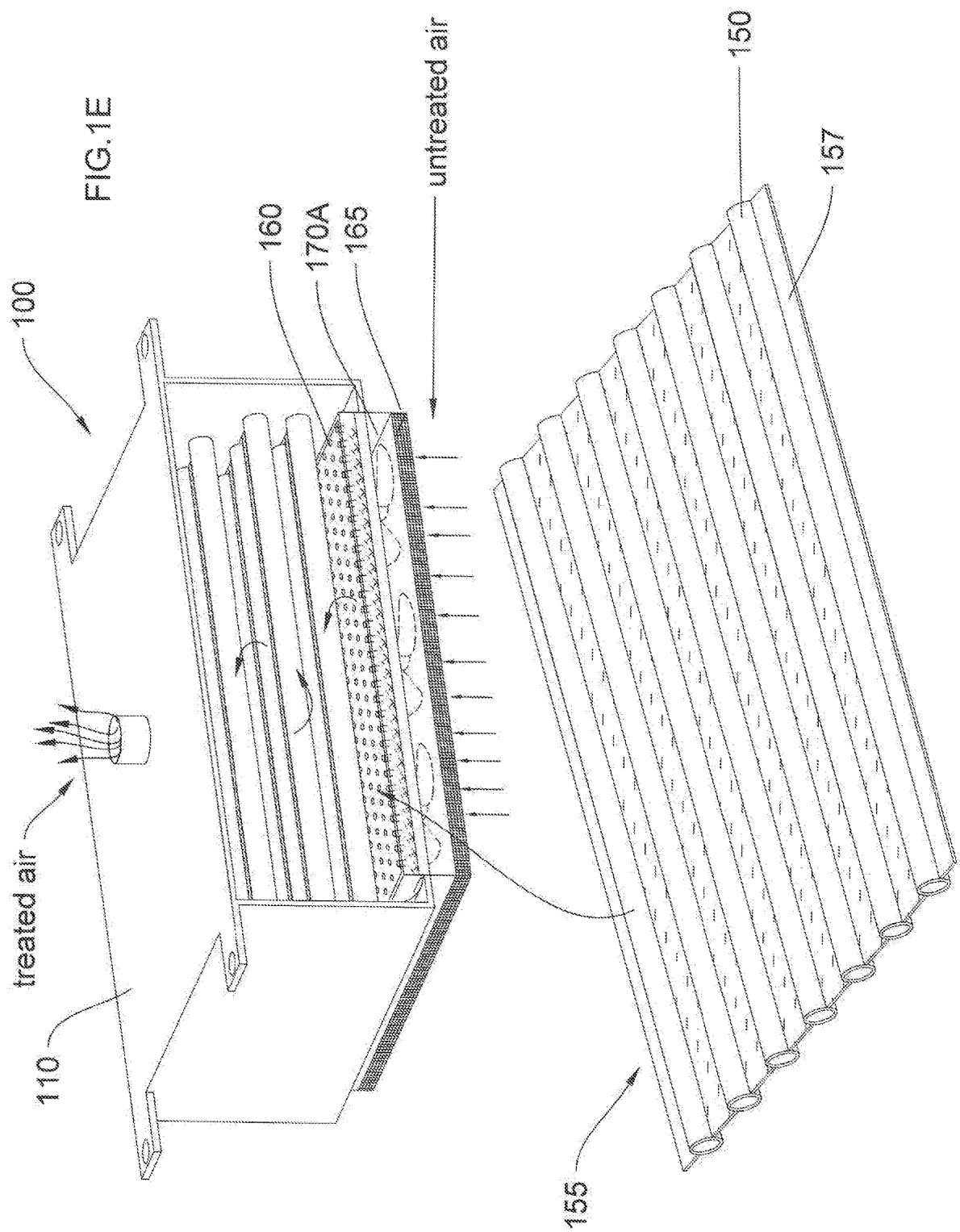

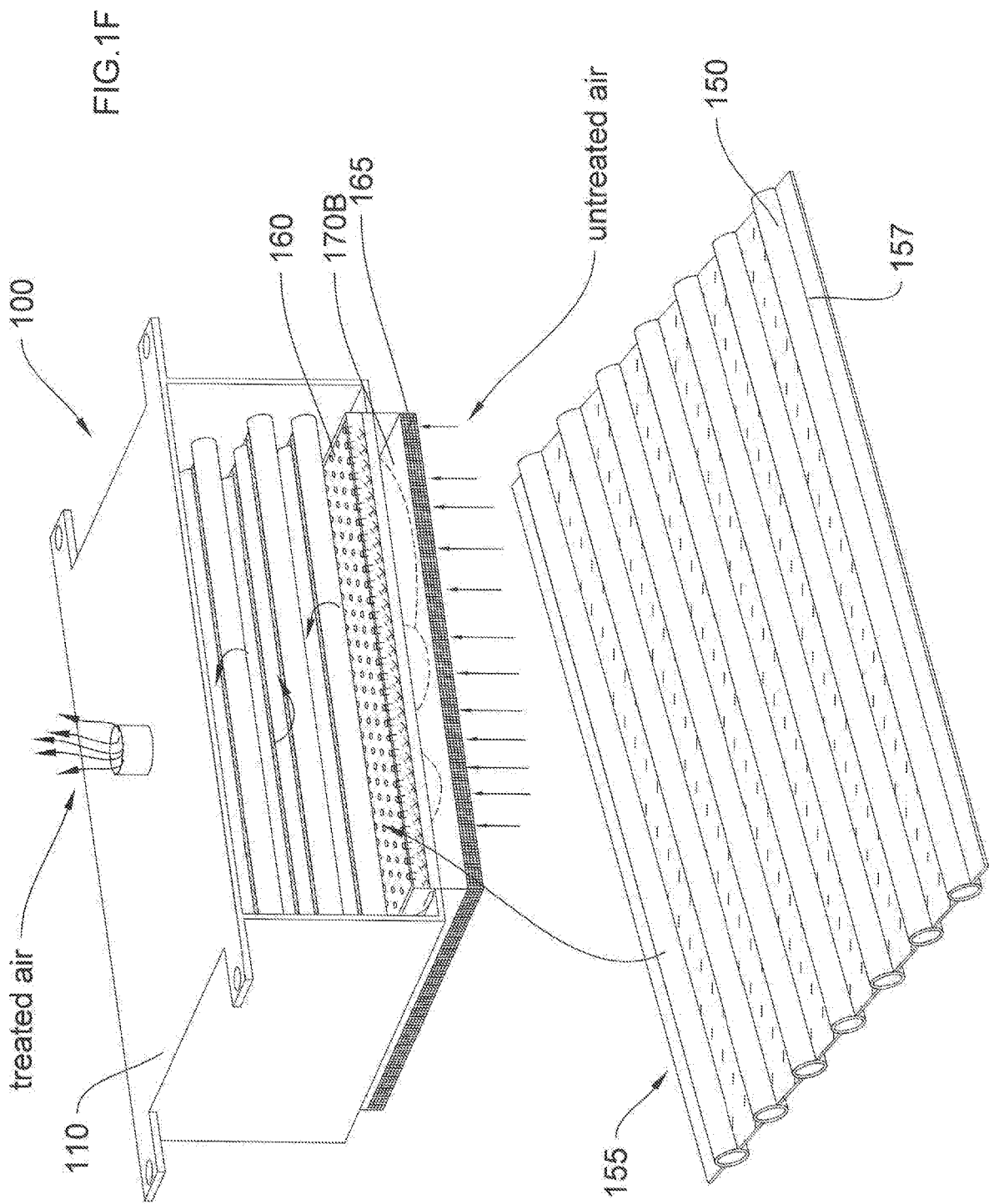

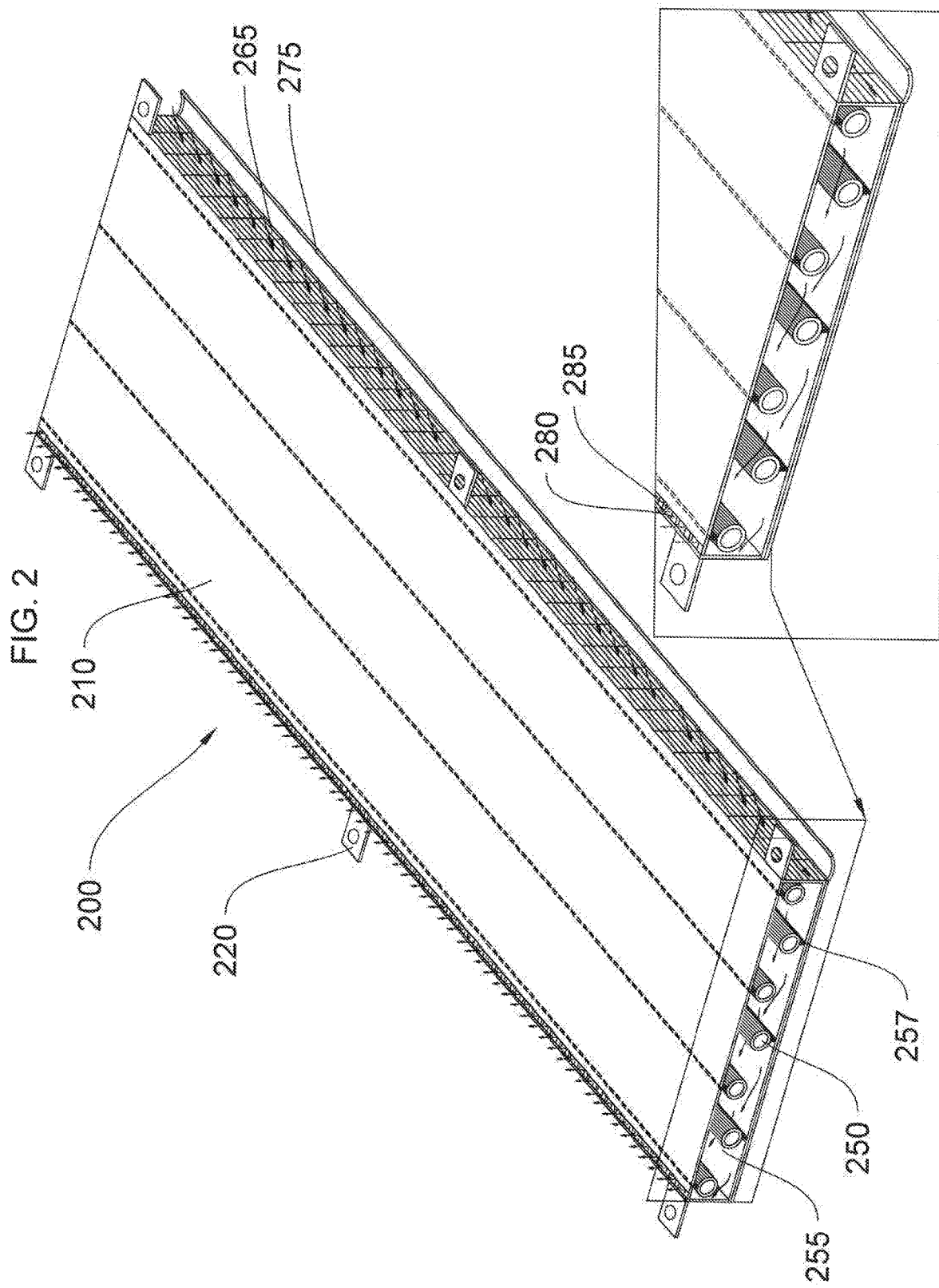

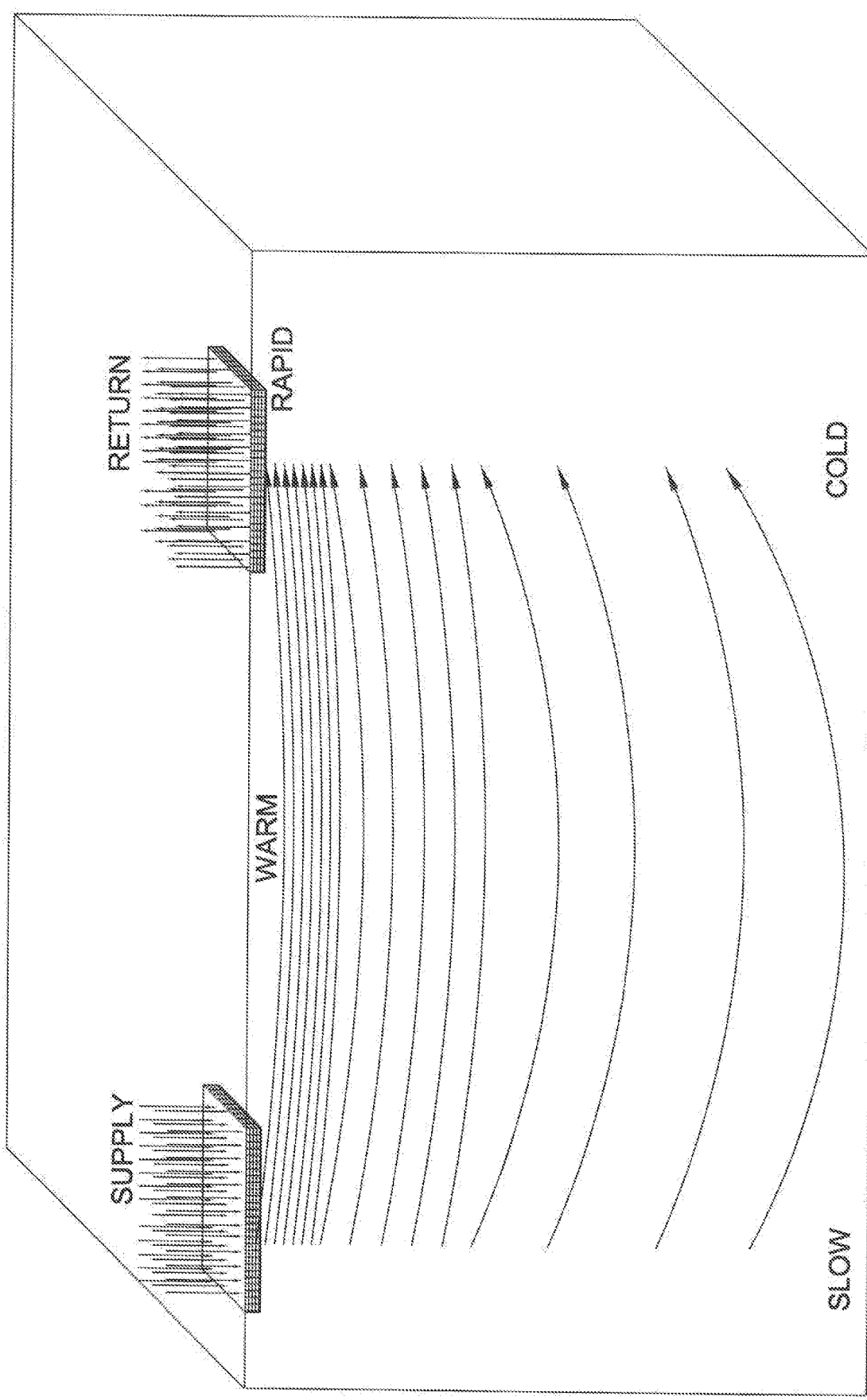

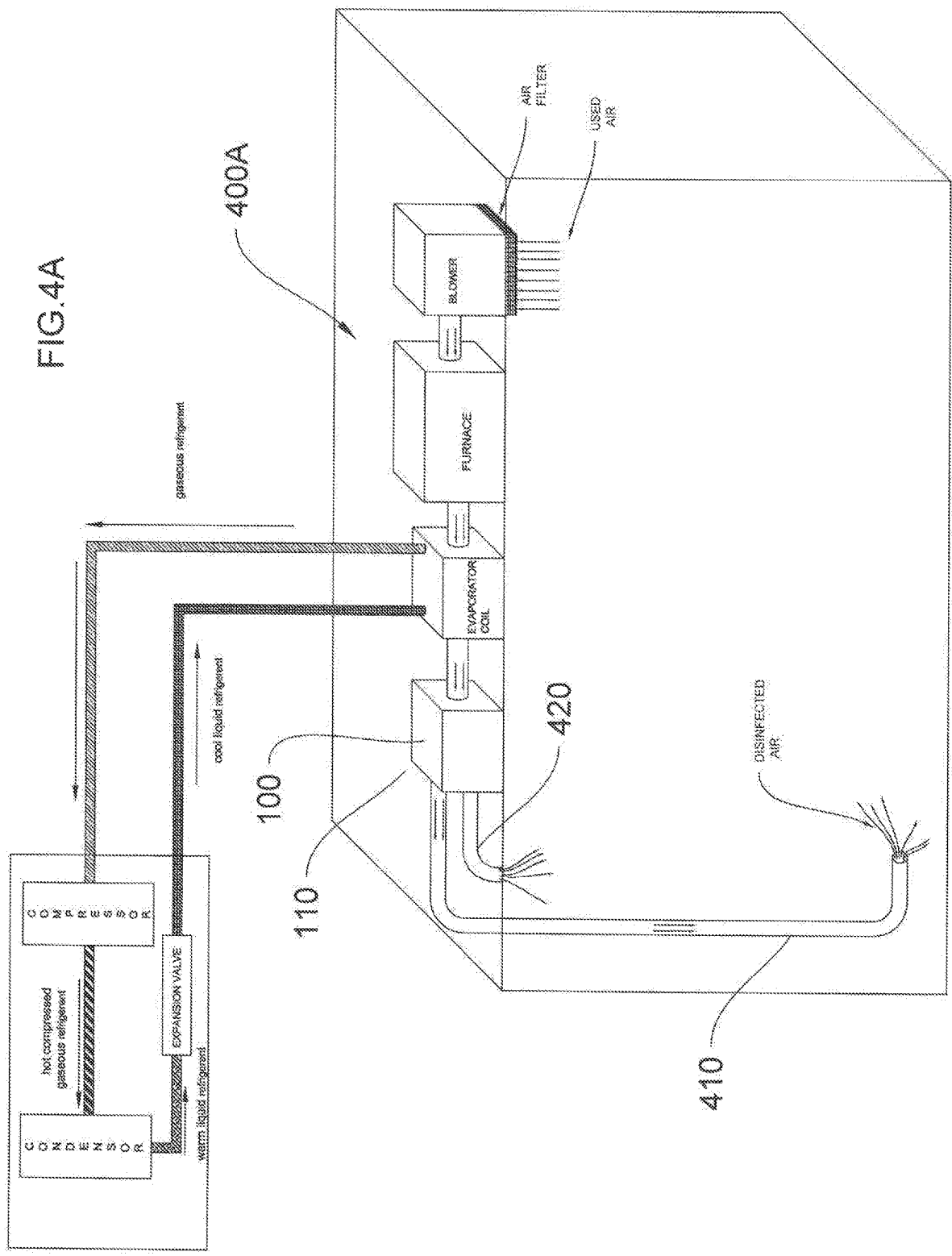

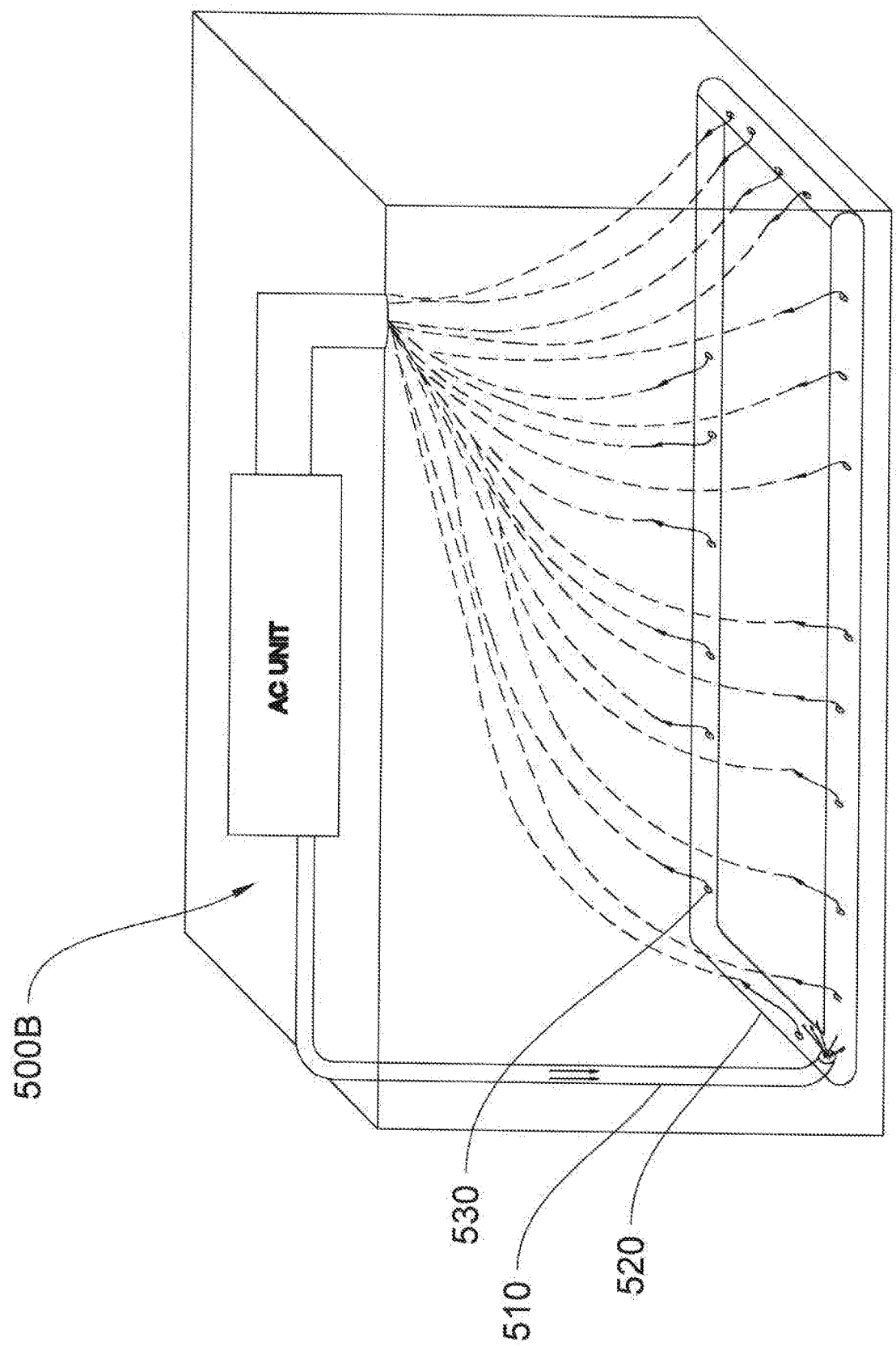

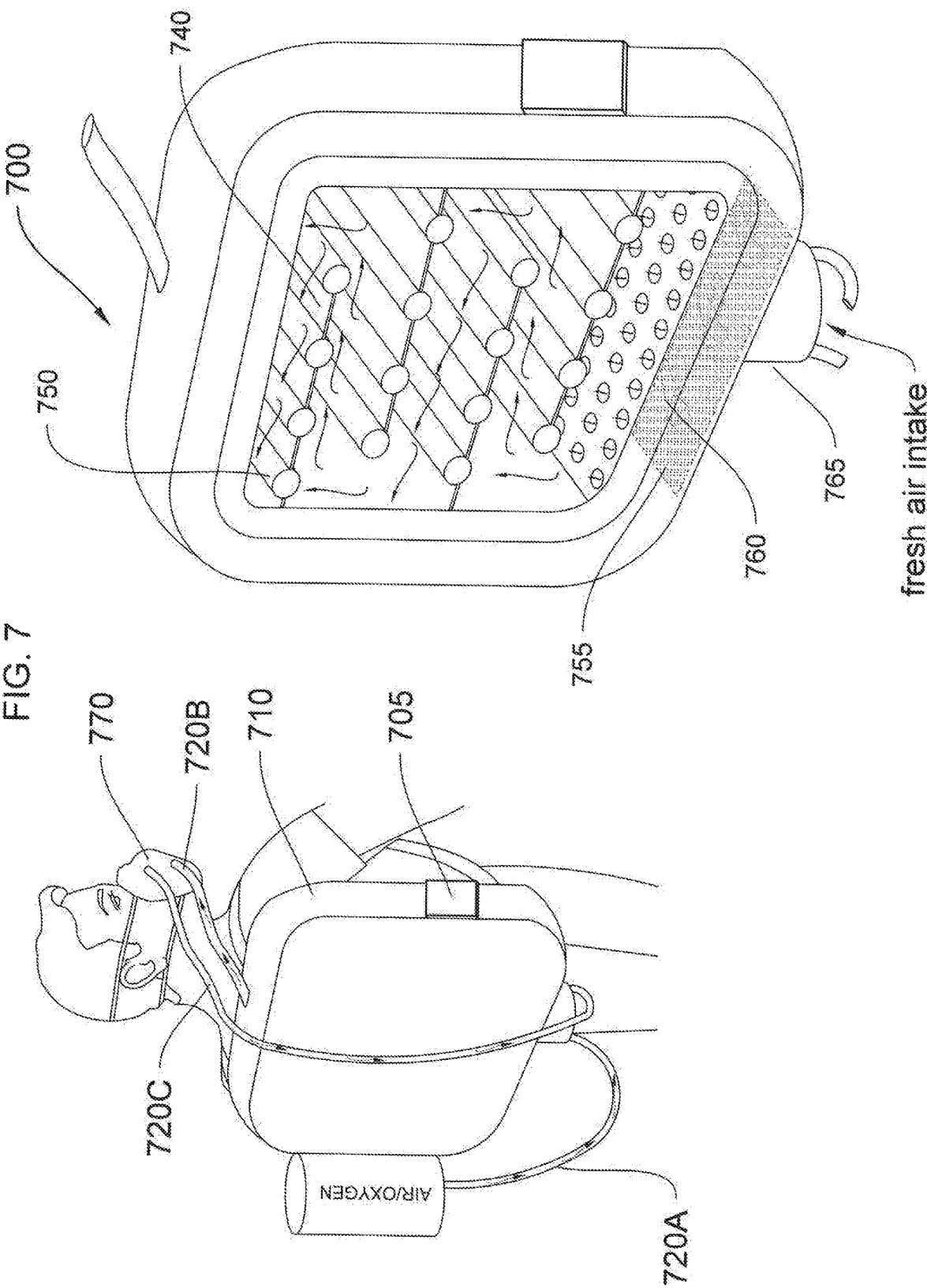

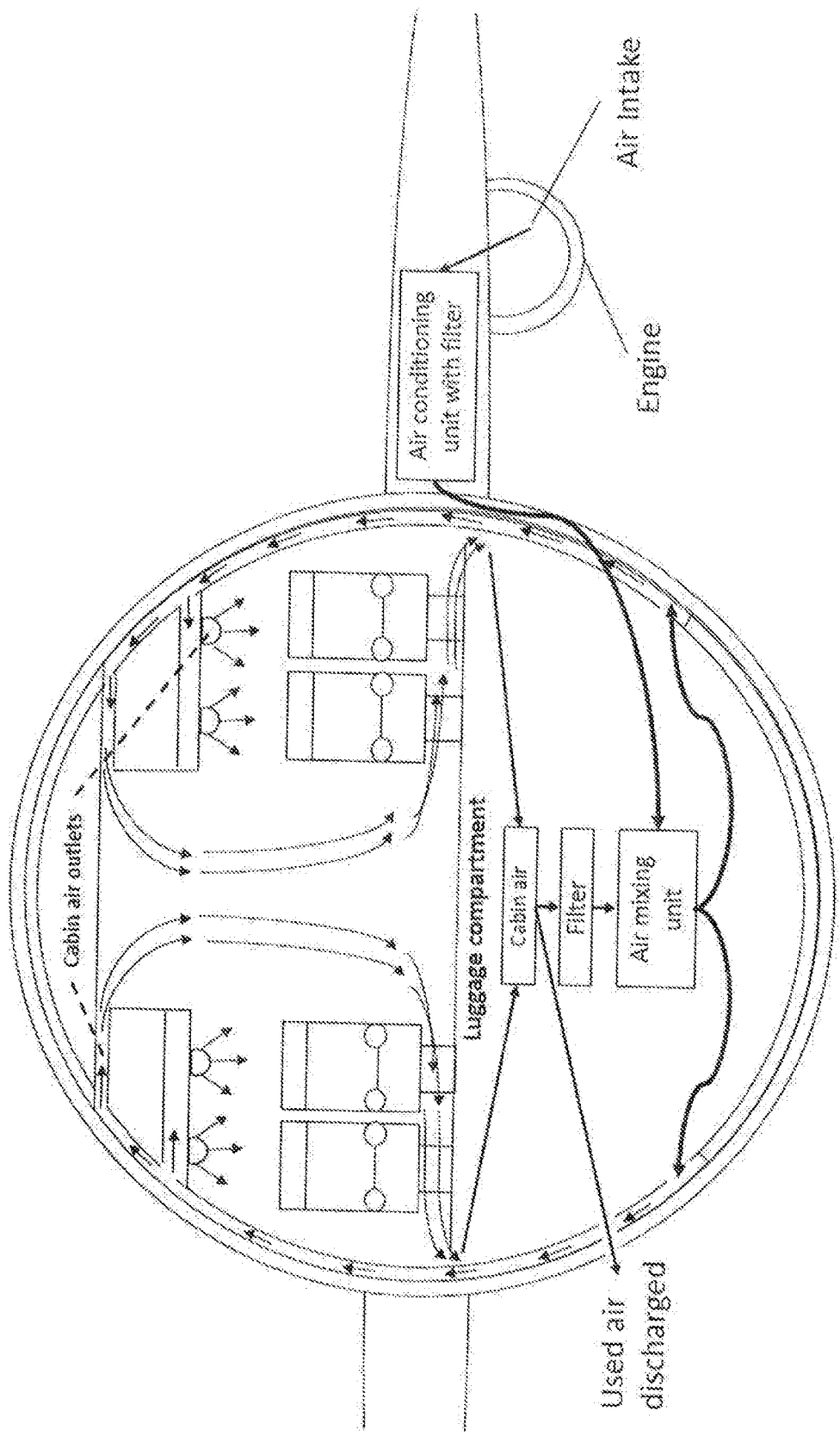

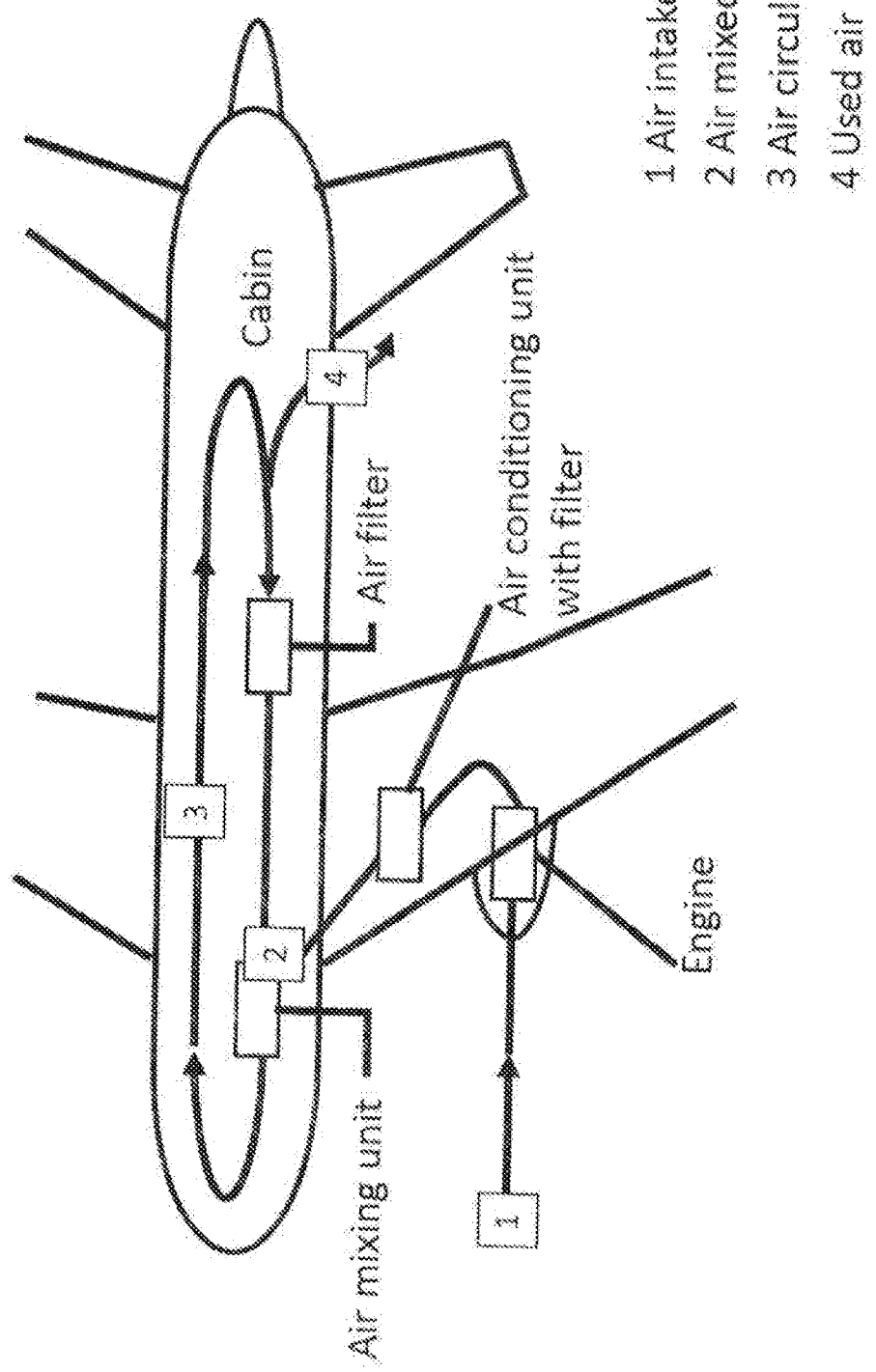

SYSTEMS, APPARATUS AND METHODS FOR PURIFYING AIR

CROSS-REFERENCE TO RELATED APPLICATIONS

This application claims priority from U.S. Provisional Patent Application Ser. No. 63/022,307 filed on May 8, 2020 and U.S. Provisional Patent Application Ser. No. 63/029,290 filed on May 22, 2020, the entire disclosures of which are part of the disclosure of the present application and are hereby incorporated by reference in their entireties.

BACKGROUND

The present invention relates to air purification, and in particular, to the elimination of harmful airborne organisms, such as, viruses and bacteria.

The use of personal protection equipment, such as, masks and face shields, is extremely important to protect healthy individuals and control the rate of spread of airborne viruses, such as, COVID-19. However, recent studies have found that COVID-19 spreads not only through personal contact but also through the air. Individuals in confined/enclosed spaces are constantly exposed to this deadly virus every time they inhale. There is a need for novel and innovative solutions to control the spread of COVID-19. The inventor posits that COVID-19 "infects" or contaminates structures in addition to infecting individuals. Therefore, innovative solutions are needed for "decontaminating" the buildings in addition to protecting individuals. Decontaminating the buildings and protecting individuals can be accomplished by continually purifying and decontaminating the air in structures, such as, buildings, airplanes, and the like. This can reduce or eliminate the spread of the COVID-19 virus and allow governments to remove lockdowns and restrictions on the movement and gathering of people in confined spaces, such as, restaurants.

The use of ultraviolet (UV) light as a disinfection means is well known in the art. Many UV light emitting devices are available in the marketplace. These devices are used to "sterilize" surgical suites, airports, and other such spaces. However, UV light should not be allowed to come near hands or other area of the skin as UV radiation can cause skin irritation. UV light is a radiation beyond the wave length of the violet rays and as such beyond the spectrum that the human eyes can see. The UV light itself has a spectrum ranging from a 100 nanometer to 400 nanometers. UV of wavelength from 315 to 400 is called UV-A, from 280 to 315 UV-B, from 200 to 280 UV-C. Far UV-C light has a spectrum ranging from 207-222 nanometers. The ozone layer blocks the UV-C but allows UV-A and UV-B to reach earth. The shorter the wavelength, the less penetration into the human skin. UV-A and UV-B can damage human skin and are the ones implicated in sunburn skin cancer, and increased risk of cataract. UV-C from the sunlight cannot normally reach the earth because of the ozone filter. Far UV-C and UV-C light cannot penetrate deep into the skin. Far UV-C light, in particular, can target the RNA/DNA of microorganisms, causing cell death or making reproduction impossible. For the purposes of this application, the terms "UV-C/UVC/far UV-C/far UVC" are used interchangeably herein.

Organisms, such as, viruses, bacteria, and other such pathogens (hereinafter referred to interchangeably as "microorganisms") that cause diseases, thrive in confined areas/spaces. The use of UV radiation for destroying the previous generations of viruses, such as, coronavirus has been attempted in the past. However, the results were not conclusive. This is because the UV has to be strong enough to destroy the virus and such high energy UV can injure the human normal cells like skin, cornea, and other cells. Additionally, the viruses have to be exposed to the UV light for a sufficient duration before they can be neutralized.

Social distancing and the use of personal protective equipment have been recommended to control the spread of airborne viruses, such as, COVID-19. However, these measures may not be sufficient to contain their spread especially in confined spaces. There is, therefore, a need for reliable techniques to destroy airborne pathogens and control their spread in confined air-conditioned spaces using UV-C radiation and modifications in the HVAC systems.

SUMMARY

The quality of air inside an indoor (or confined) space is a function of the type and performance of an installed heating, ventilating and air conditioning (HVAC) system (also herein referred to interchangeably as "air conditioning system"). These systems typically recirculate air within a closed indoor environment, control indoor temperature and conserve energy. Current air conditioning systems are configured to cool air (or heating systems are configured to heat air) that is already present within the confined unit. Cold, dry air in a confined unit provides an ideal ground for viruses to stay active.

According to an embodiment, an apparatus for disinfecting air-conditioned airflow in a confined space, comprises: a modular housing; and a disinfection chamber enclosed within the housing. A plurality of disinfection sheets are enclosed within the disinfection chamber. Each disinfection sheet comprises a plurality of ultraviolet (UV) light sources. The airflow is configured to be routed along a serpentine pathway within the housing to expose microorganisms in the airflow to far UV-C light emitted by the UV light sources for an extended and optimal duration. In one embodiment, the housing comprises a substantially box-shaped structure including top and bottom walls, opposing front and rear walls and lateral sidewalls. The box-shaped structure encloses an internal cavity or a disinfection chamber. The disinfection sheets are arranged inside the disinfection chamber. An inside surface of each of the walls may be lined with a reflective material to reflect irradiating light from the UV light sources back into the disinfection chamber.

The disinfection sheets further comprise at least: (i) a first disinfection sheet, wherein a first end of the first disinfection sheet is removably fitted to an inside surface of a first sidewall, wherein a second end of the first disinfection sheet is configured such that it is proximal to but does not contact an inside surface of a second sidewall, wherein the second sidewall is opposite the first sidewall, and wherein a first airflow gap is created in the opening between the second end of the first disinfection sheet and the inside surface of the second sidewall; (ii) a second disinfection sheet, wherein a first end of the second disinfection sheet is removably fitted to the inside surface of the second sidewall, wherein a second end of the second disinfection sheet is configured such that it is proximal to but does not contact the inside surface of the first sidewall, wherein a second airflow gap is created in the opening between the second end of the second disinfection sheet and the inside surface of the first sidewall; and (iii) a third disinfection sheet, wherein a first end of the third disinfection sheet is removably fitted to the inside surface of the first sidewall, wherein a second end of the third disinfection sheet is configured such that it is proximal to but does not contact the inside surface of the second sidewall, wherein a third airflow gap is created in the opening between the second end of the third disinfection sheet and the inside surface of the second sidewall. The serpentine airflow pathway is configured around the first, second, third, and a subsequent airflow gap. This arrangement is continued for multiple layers, as needed, to provide a sufficient length and duration of contact between the organism and the far UV-C light.

The apparatus further comprises a plurality of small-diameter tubules embedded within a base of the housing, wherein the tubules are configured to allow passage of the airflow while avoiding leakage of the far UV-C light outside the apparatus. The tubules may be substantially V-shaped.

The apparatus further comprises a High Efficiency Particulate Air (HEPA) filter. The HEPA filter is located proximal to the base of the housing.

The apparatus further comprises one or more fans, wherein the one or more fans are placed between the base of the housing and the HEPA filter, and wherein the one or more fans are configured to either force the airflow into or force the airflow out of the cavity through the tubules.

In another embodiment, the disinfection sheets are substantially V-shaped, and wherein the UV light sources are arranged in one of a horizontal or a vertical orientation. The V-shaped disinfection sheets further comprise at least: (i) a first V-shaped disinfection sheet, wherein a first end and a second end of the first V-shaped disinfection sheet are removably fitted to the front wall of the housing, wherein a first airflow gap is created between the first V-shaped disinfection sheet and the rear wall of the housing; (ii) a second V-shaped disinfection sheet, wherein a first end and a second end of the second V-shaped disinfection sheet are removably fitted to the rear wall the housing, wherein a second airflow gap is created between the second V-shaped disinfection sheet and the front wall of the housing; and (iii) a third V-shaped disinfection sheet, wherein a first end and a second end of the third V-shaped disinfection layer are removably fitted to the front wall of the housing, wherein a third airflow gap is created between the third V-shaped disinfection sheet and the rear wall of the housing. The serpentine airflow pathway is configured around the first, second, third and a subsequent airflow gap. This arrangement is continued for multiple layers, as needed, to provide a sufficient length and duration of contact between the organism and the far UV-C light.

In one or more embodiments, each disinfection sheet further comprises a plurality of removable transparent connectors. A UV light source in a disinfection sheet is connected to an adjacent UV light source by the transparent connector.

The UV light sources can be tubular. However, other shapes and configurations are also encompassed within the scope of this invention including a flat mirror-like plate.

In another embodiment, the housing comprises an outer cylindrical structure enclosing an internal disinfection chamber/cavity, and wherein a first disinfection sheet is arranged around an inside surface of the housing. An inner cylindrical member is arranged inside the internal cavity, wherein a second disinfection sheet is arranged around an outer surface of the inner cylindrical member. The apparatus further comprises an airflow diverter. The airflow diverter is arranged in a spiral or helical pattern in an opening formed between the first disinfection sheet and the second disinfection sheet. The arrangement of the airflow diverter creates the serpentine airflow pathway.

According to another embodiment, an apparatus for disinfecting an airflow, comprises: a modular box-shaped housing; and a disinfection chamber within the housing. A disinfection layer is positioned in the disinfection chamber. The disinfection layer comprises a plurality of tubular UV light sources, wherein at least: (i) a first UV light source is arranged along an inside surface of the top of the housing; (ii) a second UV light source is arranged along an inside surface of the base of the housing; and (iii) a third UV light source is arranged along the inside surface of the top of the housing, wherein the airflow is configured to be routed along a serpentine pathway created between the at least first, second and third light sources such that microorganisms in the airflow are exposed to far UV-C light emitted by the UV light sources for an extended and optimal duration. Optional disinfection sheets can be subsequently arranged in a similar manner as the first, second and third disinfection sheets to facilitate further disinfection of airflow.

According to yet another embodiment, a personal use air disinfection system involves: a wearable apparatus, wherein the wearable apparatus comprises: a housing encasing a disinfection chamber. The disinfection chamber comprises a plurality of disinfection sheets. Each disinfection sheet comprises a plurality of ultraviolet (UV) light sources emitting germicidal far UV-C light. A first pipe is configured to provide a fresh air-oxygen supply from a source, such as, an oxygen canister to the wearable apparatus. A first end of the first pipe is connected to the canister. A second end of the first pipe is connected to an inlet of the wearable apparatus. The air is configured to traverse along a serpentine pathway within the wearable apparatus to expose microorganisms in the air to the far UV-C light for an extended and optimal duration. Disinfected air is provided to the user via a second pipe connected to a filtration/protection device, such as, a medical grade mask or a face shield worn by the user. A first end of a third pipe is connected to the mask while a second end of the third pipe is connected to the inlet of the wearable apparatus. The third pipe is configured to route exhaled air from the mask to the inlet of the wearable disinfection where it is added to the air-oxygen mixture coming from the canister and is again routed for disinfection in the disinfection chamber. The recirculation of the exhaled air makes the whole system a closed circuit whereby the user does not have to inhale any ambient air. The air from the first and third pipes are routed to the disinfection chamber via a filter (such as, a HEPA filter). The air is pushed into the disinfection chamber by one or more fans located at the mouth of the disinfection chamber.

According to another embodiment, a process for recirculating air in a confined space, comprises: providing an air duct, wherein a first end of the air duct is fluidly connected to a conventional attic-based HVAC system, and wherein a second end of air duct is connected to an airflow supply vent located at or near a floor of the confined space; supplying a stream of heated/cooled air to the confined space through the supply vent; and routing used air from the confined space to the HVAC system through a return vent positioned at or near a ceiling of the confined space. The supply vent is connected to a secondary air duct, wherein the secondary air duct is arranged along a perimeter of the floor, and wherein the secondary air duct comprises a plurality of secondary vents for supplying the heated/cooled air.

According to another embodiment, a process for disinfecting a recirculated airflow in a confined space comprises: providing an apparatus for disinfecting an air-conditioned airflow as disclosed in the one or more embodiments described herein, wherein the apparatus is fluidly connected to a conventional HVAC system, and wherein the airflow is treated with germicidal UV-C light inside the apparatus; supplying a stream of disinfected heated/cooled air to the confined space through a supply vent located at or near a floor of the confined space; and routing used air from the confined space through a return vent positioned at or near a ceiling of the confined space. The supply vent is connected to a secondary air duct, wherein the secondary air duct is arranged along a perimeter of the floor, and wherein the secondary air duct comprises a plurality of secondary vents for supplying the heated/cooled air. The return vent is configured to route substantially all the used air to the atmosphere. Alternately, the return vent is configured to route at least a portion of the used air back to the apparatus for disinfection.

According to another embodiment, the air inside an airplane is purified either by: (i) disinfecting recirculated cabin air within the apparatus for disinfecting air disclosed herein, or (ii) entirely avoiding the recirculation of used cabin air. The air purification process involves connecting a bi-directional valve to an airplane's air mixing unit. When the bi-directional valve is in an open position, the contaminated/used cabin air is continually discarded outside the airplane while fresh air is continually drawn in to the airplane though its engine turbines. Under these conditions, recirculation of used cabin air is completely avoided and the air entering the cabin is totally fresh atmospheric air. Alternately, the cabin air can be treated with the apparatus for disinfecting air, as disclosed herein. In this embodiment, the bi-directional valve is closed. Used cabin air is filtered with a HEPA filter and routed to the apparatus. The apparatus can destroy the organisms that are not filtered. The filtered, disinfected mixture of fresh air and the used cabin air can now be safely sent back to the cabin. In certain embodiments, a measured amount of used cabin air can be released by leaving the bi-directional valve in at least a partially open state. By partially opening the bi-directional valve, the load on the apparatus can be reduced.

In yet another embodiment, a process for heating and cooling a confined space without using a HVAC system, comprises: overlaying piping means for transporting heated or cooled water along sidewalls, floor and ceiling areas in the sheetrock of the confined space, wherein the piping means include: (i) a first larger diameter pipe for transporting heated or cooled water; (ii) a plurality of smaller diameter pipes, wherein the smaller diameter pipes carry the transported heated or cooled water from the larger diameter pipe along the sidewalls, floor and ceiling areas of the confined space; and (iii) a second larger diameter return pipe for collecting the water from the smaller diameter pipes. The process further comprises providing a controller for heating or cooling the water and pumping it into the circulation.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The accompanying drawings, which are incorporated into and form a part of the specification, illustrate various embodiments of the present invention and, together with the description, serve to explain the principles of the invention. The drawings are only for the purpose of illustrating exemplary embodiments of the invention and are not to be construed as limiting the invention. In the drawings:

FIGS. 1A-1D illustrate multiple views of an apparatus for disinfecting air-conditioned airflow according to an embodiment.

FIG. 1E illustrates an apparatus for disinfecting air-conditioned airflow having multiple fans according to another embodiment.

FIG. 1F illustrates an apparatus for disinfecting air-conditioned airflow having a single fan according to another embodiment.

FIG. 2 illustrates an apparatus for disinfecting air-conditioned airflow according to another embodiment.

FIG. 3 illustrates typical air flow patterns in a confined space having supply and return vents on the ceiling.

FIG. 4A illustrates a system for routing disinfected air to the floor of a confined space according to an embodiment.

FIG. 5B illustrates a system for routing air-conditioned airflow to the floor of a confined space according to another embodiment.

FIG. 7 illustrates a personal use air disinfecting system according to an embodiment.

FIGS. 8A-8B illustrates a conventional air conditioning system in an aircraft according to an embodiment.

DETAILED DESCRIPTION

Figure 1G:
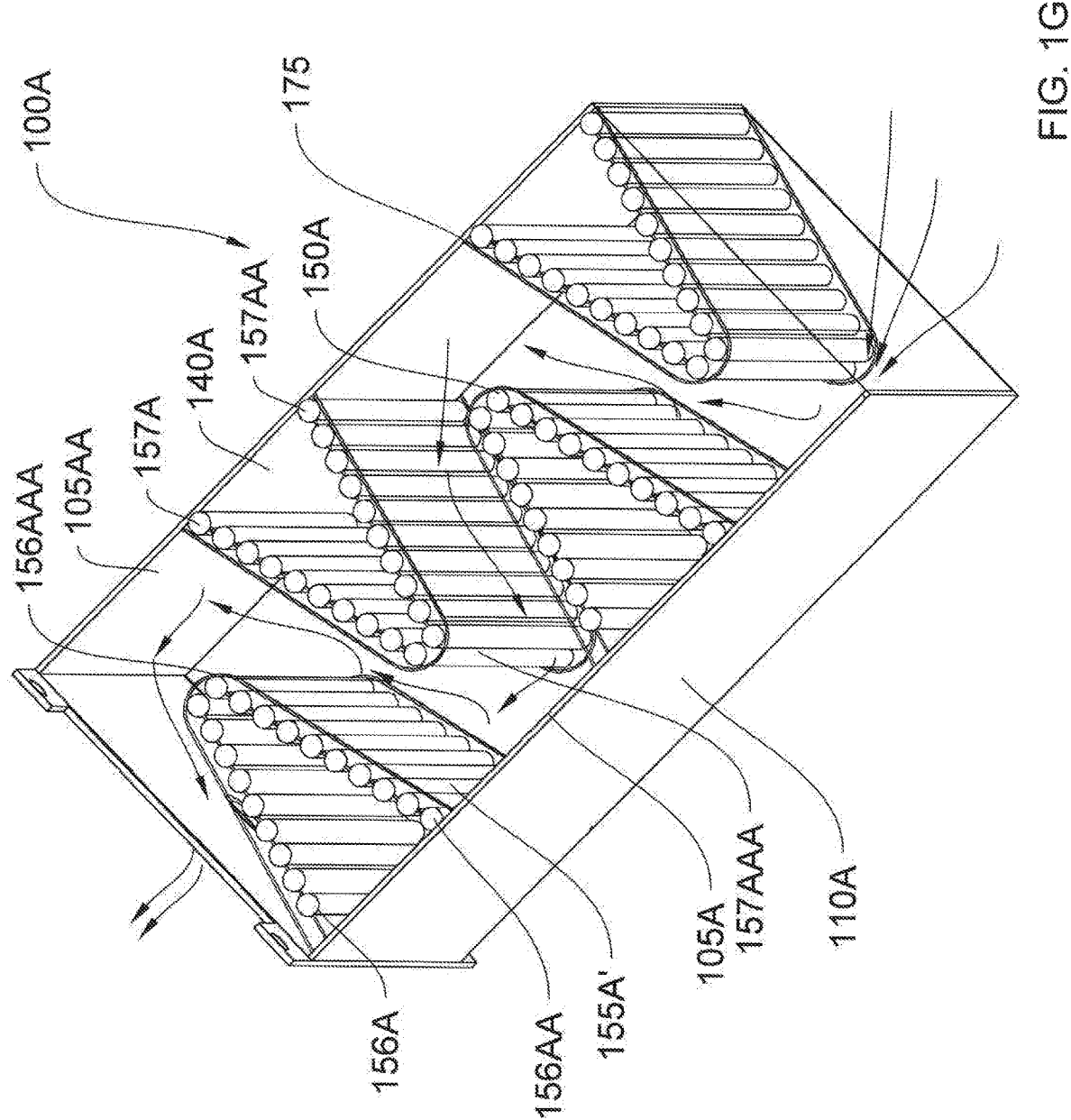
FIG. 1G illustrates an apparatus for disinfecting air-conditioned airflow according to an embodiment.

Systems, apparatus and methods are described herein for disinfection of airflow from an air-conditioning system to substantially kill or eliminate SARS-CoV-2 virus and other similar airborne micro-organisms that cause COVID-19. The air-conditioned airflow is disinfected using a UV light source. Preferably, the UV light source is configured to emit germicidal far UV-C or UV-C radiation. The UV light sources are tubes, either straight or turned into more compact shapes, which can be transparent. The UV light sources can also include, without limitation, UV lamps, UV lasers, UV LED lights and other similar sources. In some embodiments, the UV light source can include a flat mirror-like plate. Far UV-C/UVc light/radiation can be used to disinfect the airflow without harming the human body/eyes by encasing them in UV protected enclosures and/or keeping them away from human habitats. This makes it suitable for the one or more embodiments discussed herein.

The present invention can be utilized in any confined space. As used herein, the term "confined space" can include any enclosed or indoor space. The confined space can include, without limitation, rooms, hotels, restaurants, homes, warehouses, nursing homes, hospitals, clinics, laboratories, office buildings, buses, places of worship, malls, schools, theaters, sports arenas, aircrafts, trains, subways, yachts, cruise ships, and other similar enclosed spaces. The confined space can be equipped with one or more air conditioning systems. Thus, one or more embodiments of the present invention are configured to disinfect air-conditioned airflow in confined spaces.

In one embodiment, the apparatus of the present invention can be configured to be attached to or incorporated as part of existing air conditioning systems and do not require any significant modification to these units. In typical "split" HVAC systems (comprising an outdoor unit having a condenser and compressor and an indoor unit connected to the evaporator furnace and a blower), the apparatus can be in fluid communication with an indoor blower. According to one or more embodiments, the blower/furnace are attic-based or located in a space just below the roof of the confined space. In a "packaged" air conditioning system, the blower is located close to a compressor and is located outside the confined space. In packaged systems, the apparatus can be configured to be in fluid communication with the external blower. In multi-level confined spaces, such as buildings with multiple floors, having blowers in individual rooms, the apparatus can be incorporated into the individual blowers. In one or more embodiments, the apparatus can also be compressed to the size of a briefcase and can be attached to the air inlet or outlet of any confined space.

Multiple views of an apparatus 100 for disinfecting air-conditioned airflow are illustrated in FIGS. 1A-1D. As used herein, the term "disinfecting" is used to mean sanitizing or treating an incoming (filtered or unfiltered) airflow such that it is substantially free of harmful microorganisms. In some embodiments, the apparatus is configured to also filter out particulates.

The apparatus 100 includes a compact modular housing 110. The housing 110 can be provided in a stand-alone configuration for attachment to an exhaust window (or, an outlet) and/or a blower (or, an inlet), or can be incorporated in line with a split air-conditioning system (not shown). A similar arrangement can be incorporated into the packaged air conditioner also. The housing 110 comprises of a box-shaped enclosure/structure having panels 112 on its top and bottom surfaces, left and right opposing sidewalls/surfaces and front and back surfaces. The panels 112 can be made of aluminum, steel, fiberglass, carbon, or any other suitable material, that can completely block the UV light coming out of the device. A front panel is not shown in the accompanying figures merely to illustrate the internal components of the apparatus 100. The panels 112 enclose an internal cavity 140 or disinfection chamber having various components for disinfecting air-conditioned airflow. The terms "air" and "airflow" are used interchangeably herein.

The housing 110 can be secured or anchored to the inlet or outlet of the air-conditioning system, in an enclosed space like a room, with brackets 120. The apparatus 100 can further include a docking pipe 130 that can be coupled to the inlet or outlet of an air-conditioning system (not shown). The apparatus 100 can be placed on the ceiling, within a wall or located out of view in the attic. The apparatus 100 can be configured to allow the passage of air entry through a bottom surface of the housing 110, in the outlet unit, or reverse in the inlet unit.

The cavity 140 contains a disinfection chamber. A plurality of tortuous/convoluted passages 180 are formed in the disinfection chamber. These air passages are formed by a unique arrangement of multiple disinfection/treatment sheets 155 within the cavity 140. The disinfection sheets 155 include a plurality of germicidal UV light sources 150 connected to each other by transparent bridge-like connectors. The panels 112 can be made opaque to prevent UV leakage.

A first end of a first disinfection sheet 155A is configured to be removably fitted to a channel 159 formed on an inside surface of a first sidewall 110A. The second end of the first disinfection sheet 155A is proximal to but does not touch an inside surface of the opposite second sidewall 110B. A small airflow gap 102A is, therefore, formed in the space between the second end of the first disinfection sheet 155A and the sidewall 110B. Similarly, a first end of an adjacent/second disinfection sheet 155B is configured to slidably be fitted to a channel (not shown) formed on the inside surface of the second sidewall 110B while leaving a small airflow gap 102B between its second end and the opposing first sidewall 110A. The other disinfection sheets are arranged in a similar manner, that is, a first end of a third disinfection sheet 155C can slide into a channel formed on the first sidewall 110A leaving an airflow gap 102C between its second end and the second sidewall 110B, and so on. This arrangement provides a sufficient length and duration of contact between the organism and the far UV-C light. The disinfection sheets 155 can be conveniently removed, if needed, for maintenance or replacement purposes. This arrangement creates a serpentine airflow pathway around the airflow gaps 102A, 102B, 102C . . . , and causes the air to be forced to go over each of the disinfection sheets before it exits the apparatus 100. The air may include harmful microorganisms.

The UV light sources 150 are configured to emit germicidal far UV-C light. Far UV-C light can penetrate the cell walls of the microorganisms and cause cellular or genetic damage. The affected microorganisms are, therefore, killed and/or become unable to reproduce. Aside from the intensity of the UV-C light, their exposure time to the UV-C light is a key factor in determining how efficiently the microorganisms are disabled. Advantageously, the serpentine airflow path of the present invention ensures that the microorganisms are exposed to the UV-C light for a length of time that is sufficient to kill or disable them. As such, the air exiting the apparatus is substantially disinfected, that is, free of these harmful microorganisms. The apparatus 100 can be connected to an electrical outlet and can be turned on or off, as needed.

The base panel 112A includes a plate 114. Multiple fine-diameter, substantially V-shaped opaque hollow miniature tubes or tubules 160 are embedded in the plate 114 in a slanted/oblique arrangement. The arrangement of these opaque tubules 160 in a V shaped arrangement ensures that air gets in or leaves through the tubules, but the far UV-C light is prevented from leaking/coming back out. This can protect humans in the vicinity of the apparatus 100. In another embodiment (not shown), a flat plate can be attached outside the unit 110 such that substantially any leakage of the far UV-C light is blocked.

As shown in FIG. 1C, the tubules force/direct untreated air into the cavity 140. The air flows in a serpentine manner over the disinfection sheets 155 where it is exposed to far UV-C light emitted by light sources 150. The disinfected/ treated air exits through the docking pipe 130. In an alternate embodiment, as shown in FIG. 1D, untreated air flows into the housing 110 through the docking pipe 130, flows in a serpentine manner over the disinfection sheets 155 where it is exposed to far UV-C light emitted by light sources 150. The disinfected/treated light exits through the multiple fine-diameter tubules 160 embedded in the plate 114.

As illustrated in FIGS. 1B and 1E-1F, each disinfection sheet 155 comprises a plurality of UV light sources 150. In an embodiment, the UV light source 150 includes an outer casing having a channel/slot 159 for slidably receiving a bridge-like connector 157. This facilitates the convenient removal and replacement of a single UV light source 150. The individual tubes in light source 150 can also be pulled out and replaced as in FIG. 1B. The connectors 157 are configured to be transparent such that the far UV-C light can penetrate through the subsequent layers of the disinfection sheets. This ensures optimal disinfection of the airflow as it flows through the apparatus. The connectors 157 can be made of quartz, plastic, or another suitable transparent material.

As shown in FIGS. 1E-1F, the apparatus 100 includes a High Efficiency Particulate Air (HEPA) filter 165. HEPA filters are known in the art. The HEPA filter 165 is configured to filter particulates and microorganisms from entering the cavity housing the UV light sources. This can prolong the life of the apparatus 100 and reduce the need for it to be cleaned frequently. The filter 165 can be periodically checked and if necessary, it can be cleaned or replaced.

When used at the outlet of the air conditioning system, either a plurality of smaller fans 170A or a single larger fan 170B can be placed below the tubules 160 and above the filter 165. The fans 170A, 170B can be configured to force air into the cavity of the apparatus 100. This will make the air movement in confined spaces more efficient. In another embodiment, a reverse fan is used at the inlet of the air conditioning system to blow air into the room again facilitating stronger and more complete replacement of the air in the confined space with clean air. In this embodiment, the air coming into the room enters through docking pipe 130 and goes into the room through the tubules 160. The fans behave like suction units that draw air out from the apparatus 100 and push it into the confined space/room.

Figure 1H:
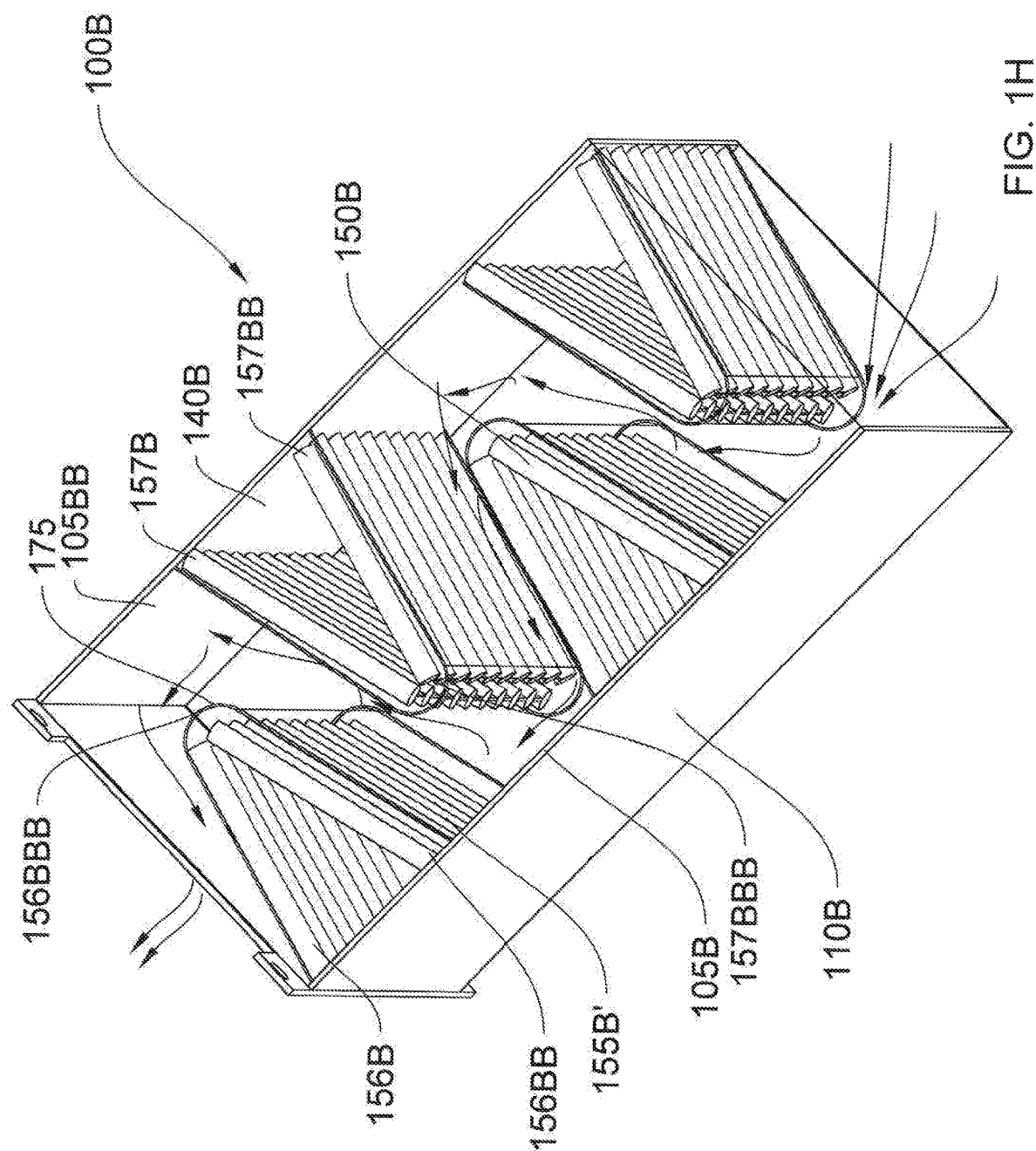
FIG. 1H illustrates an apparatus for disinfecting air-conditioned airflow according to an embodiment.

FIGS. 1G-1H illustrates another embodiment 100A, 100B of an apparatus for disinfecting air-conditioned airflow. The housing 110A, 110B includes a cavity 140A, 140B. Unlike the disinfection sheets 155 which are substantially flat and planar, the disinfection sheets 155A', 155B' are substantially V-shaped. The ends 156A, 156AA and 156B, 156BB of a first V-shaped layer are slidably fitted within grooves formed on a front wall of the housing 105A, 105B respectively while the other end 156AAA and 156BBB does not touch an inner surface of an opposing rear wall 105AA, 105BB. The ends 157A, 157AA and 157B, 157BB of an adjacent second layer are slidably positioned within grooves formed on the rear wall 105AA, 105BB while the other end 157AAA, 157BBB is not connected to an inner surface of the front wall 105A, 105B. This arrangement is continued for multiple layers, as needed, to provide a sufficient length and duration of contact between the organism and the far UV-C light. A serpentine airflow pathway is configured around disinfection sheets 155A, 155B, . . . . Each disinfection sheet 155A', 155B' includes a plurality of UV light sources 150A, 150B emitting germicidal far UV-C light. As shown in FIG. 1G, the UV light sources 150A are arranged in a horizontal orientation (or in the same plane as the base of the housing). As shown in, FIG. 1H, the UV light sources 150B are arranged in a vertical orientation (or perpendicular to the base of the housing). The UV light sources 150A, 150B may be affixed to a plate 175 made of quartz or another suitable material. The plate 175 is configured to prevent the airflow from rattling the tubes. Alternately, the UV light sources 150A', 150B' can be bridged with a transparent connector (such as, connector 157) that can conduct far UV-C light.

Figure 1I:
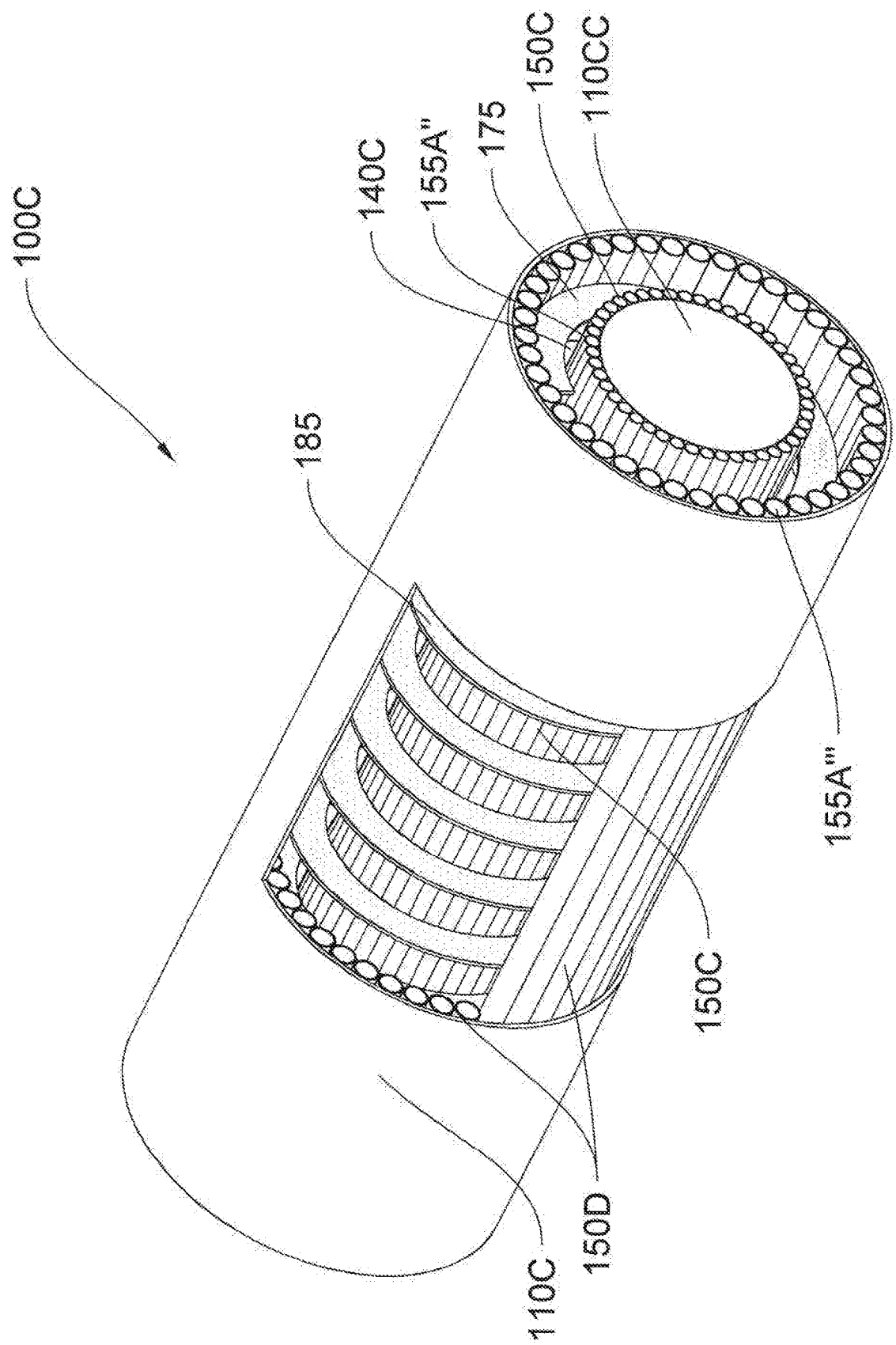
FIG. 1I illustrates a perspective view of an apparatus for disinfecting air-conditioned airflow according to yet another embodiment.

FIG. 1I illustrates another embodiment of an apparatus 100C for disinfecting air-conditioned airflow. As shown, the apparatus 100C includes a substantially cylindrical outer housing 110C. The apparatus 100C further includes a cylindrical inner housing 110CC that is positioned centrally within a cavity 140C formed within the outer housing 110C. The inner cylinder 110CC—which may be a solid/rod-like structure —extends the length of the outer housing 110C. A disinfection sheet 155A—comprising a plurality of UV light sources 150C is affixed around an outer surface of the inner cylinder 110CC while another disinfection sheet 155A— comprising a plurality of UV lights 150D is affixed to an inner surface of the outer housing 110C. The UV light sources 150C, 150D are configured to emit germicidal far UV-C light. An airflow diverter 185 is positioned in the space between the UV light sources 150C and 150D in the cavity 140C. The airflow diverter 185 is substantially spiral or helical. The airflow diverter 185 is configured to create a serpentine airflow pathway for the incoming (untreated) airflow such that any microorganisms in the air are exposed to the far UV-C lights for a substantially long period. The length and diameter of the housing 110C and the distance between each spiral turn of the airflow diverter 185 can be increased or decreased to increase or slow the passage of the airflow to be disinfected. The various embodiments of the apparatus for disinfecting air-conditioned airflow, as shown in FIGS. 1A to 1I, can be incorporated to an existing air-conditioning system.

In another embodiment, as shown in FIG. 2, an apparatus 200 for disinfecting an airflow includes a housing 210 containing a disinfection chamber. A single air disinfection layer 255 is located within the disinfection chamber. The housing 210 is substantially elongated and box-like in appearance. The air disinfection layer 255 comprises multiple UV light sources 250 for emitting germicidal far UV-C light. Each light source 250 can slidably positioned in a groove formed on an inner surface of the housing 210 using connector 257. The connector 257 can be made of glass or another suitable material. The UV light sources 250 can be positioned on the top and base of an inside surface of the housing 210 in an alternating pattern. This pattern creates a serpentine airflow pathway for an incoming airflow. The serpentine airflow pathway increases an exposure time for the microorganisms in the airflow to the UV-C light.

The housing 210 can include securing means, such as, brackets 220 for attaching the apparatus 200 to a surface (such as, the ceiling of a bus). The apparatus 200 can further include a HEPA filter 265 for filtering incoming air. The apparatus 200 further includes a flap 275 for preventing leakage of far UV-C light rays. The apparatus 200 can also be covered by an opaque shade (not shown) for preventing the UV light leakage. The housing 210 can further include support members 280 for keeping the top surface of the unit straight without bending. The support members 280 include slits 285 which can be cut along the length of the unit 210. These slits 285 are configured to vent/allow the air to leave the housing 210.

The COVID-19 pandemic has starkly illustrated the risks assumed by frontline workers, including healthcare workers. These workers often risk their own lives and the lives of their family and friends to care for patients infected with contagious viruses, such as, COVID-19 and other such viruses. Conventional personal protective equipment (PPE), such as masks or face shields, cannot offer comprehensive protection for these workers. Also, virions attached to the PPE can be released when the healthcare worker removes their PPE in a change room, causing them to get infected. FIG. 7 illustrates a portable air disinfection system 700 for personal/individual use. The system 700 can be configured to provide a continual source of disinfected air for an individual user, such as, a healthcare worker or any other user requiring additional protection through a closed circuit system.

The system 700 includes a wearable apparatus for disinfecting airflow 710. The apparatus 710 can be conveniently worn as a backpack by a user, such as, a healthcare worker. The system 700 further includes an air/oxygen source, such as, a canister, in fluid communication with the apparatus 710. A first end of a tube/pipe 720A is connected to the canister while a second end of the tube/pipe 720A is connected to the wearable apparatus 710. Air/oxygen/or a mixture of the same is drawn in through the first tube/pipe 720A and routed to an inlet 765 of the apparatus 710. A HEPA filter 755 is positioned at the base of the portable apparatus 700 to filter the incoming airflow. One or more miniature fans 760 are positioned at the mouth of a disinfection chamber 740. The fans 760 are configured to draw air into disinfection chamber 740. The chamber 740 includes multiple air disinfection sheets 740. Each air disinfection sheet 740 includes a plurality of UV light sources 750 which are configured to emit far UV-C light. As illustrated in FIG. 1, for example, the air disinfection sheets 740 are arranged in such a manner that a serpentine airflow pathway is created for the incoming air/oxygen/mixture inside the disinfection chamber 740.

The wearable apparatus 700 may have a unit 705 to hold or contain a power source. The unit 705 can accept one or more power sources such as batteries therein. The unit 705 can be removable and replaceable from the apparatus 700. The walls of the portable apparatus 700 can be made of a suitable material that can block the leakage of far UV-C light so that there is no harm done to the individual wearing the apparatus.

The air gets disinfected in the chamber 740 and the disinfected and filtered air is transported through a second pipe/tube 720B to the user. A first end of the second pipe/tube 720B is connected to the wearable apparatus while a second end of the second pipe/tube 720B is fitted within a first opening in a tight-fitting medical grade mask 770. The user can, therefore, be provided with substantially pure/disinfected air for inhalation. The exhaled air is routed from the mask 770 to the apparatus 710 by a third pipe/tube 720C. One end of the third pipe/tube 720C is fitted within a second opening in the mask 770 while a second end of the third pipe/tube 720C is connected to an inlet 765 of the apparatus 710. The exhaled air is filtered and then mixed with the air/oxygen mixture in the disinfection chamber. The filtered and disinfected air is again transported to the mask 770. For further protection, the user wearing the portable apparatus 700 can be air washed to remove any residual surface contamination before going to the change room.

Thus, the various embodiments of the apparatus for disinfecting airflow, as discussed herein, can kill or disable harmful microorganisms by utilizing the maximum strength of far UV-C light and a HEPA filter, and by adjusting the size of the apparatus and manipulating the number of air disinfection treatment sheets comprising UV light sources.

It is well recognized that when a person sneezes or even talks loudly, a fine mist of mucus and saliva droplets is expelled from their mouth. A cloud of droplets can remain suspended for several minutes, depending on the size of the droplet, the turbulence, the temperature and the humidity. If the person is infected with a virus, such as COVID-19, the droplets may also contain one or more virus particles. Large droplets, which are larger than five to ten microns, may quickly fall to the ground or on nearby surfaces. However, the smaller droplets may travel a significant distance which may be even greater than six feet. In some conditions, the small droplets, called aerosols, can quickly evaporate. The length of time before the aerosols evaporate depends on several conditions, including humidity and temperature. Healthy people can inhale the infectious droplets, or the droplets can land on their eyes, nose and mouth. People who inhale the airborne microorganisms do not need to have face-to-face contact or be in the same room as the infected person to be exposed and potentially infected by the infectious aerosols.

Studies have also shown that under normal air conditions, the droplets that fall to the ground/floor can completely dry out. The dried-out residual of droplets, which may contain infectious microorganisms, are called droplet nuclei. The light weight droplet nuclei can rise and float in the air. They can be transported significant distances in the air by typical daily activities, such as, as a result of people walking through a room. According to the inventor, the droplet nuclei are transported by movement of air from the floor to the ceiling of the confined space where they enter a "return vent" of an air conditioning duct. The return vent returns the air back to the ductwork system. These droplet nuclei are then recirculated back into the confined unit through a "supply vent" of the air conditioning duct.

According to one or more embodiments, the present invention involves a systems and processes for ensuring that the "used" air, that is returned through the return vent, is substantially discharged into the outside atmosphere. Means for delivering substantially "fresh" air from the outside/atmospheric air to the air conditioning system may also be provided such that the air supplied to the confined space through the supply vent is substantially devoid of recirculated air and airborne microorganisms and is "totally fresh air conditioning". Advantageously, in one or more embodiments, one or more supply vents are located at the floor level or substantially near the floor level while one or more return vents are located in the ceiling or substantially near the ceiling. The reverse is also possible (not shown). This is different from the majority of the conventional ventilation systems where both supply and return vents are located in the ceiling.

According to another embodiment, the present invention involves treating heating/cooled air from a conventional air conditioning system with an embodiment of the apparatus for disinfecting the airflow, as discussed above. The apparatus includes a disinfection chamber comprising a plurality of UV lights. The incoming airflow into the disinfection chamber is configured to be routed along a serpentine pathway within the housing such that microorganisms in the airflow are exposed to the germicidal far UV-C light produced by the UV light sources for an optimal duration resulting in their neutralization. The disinfected air is discharged to the AC ducts and delivered through supply vents which are located at the floor level or substantially near the floor level in each room.

As shown in FIG. 3, supply vents positioned on or substantially near the ceiling are conventionally used to deliver cold/hot air. The air is then circulated in the room. The circulated air/used air leaves the room through return vents which are also located on or substantially near the ceiling. Hot air rises while cold air sinks. The hot air in the room tries to go up towards the ceiling. Therefore, air circulation is naturally more powerful close to the ceiling and gets weaker and weaker as we go down towards the floor. This leaves cold, dry, stagnant air in the lower half of the room where people usually move around. Unfortunately, cold, dry, stagnant air is ideal for some microorganisms like the coronavirus. This makes people vulnerable to infection and possible death.

The situation is even worse in cold climates where a heater is used in the room. The hot air coming into the room stays close to the ceiling and escape through the outflow return vents. In reality, more energy is needed to heat the room because of the resistance for the hot air to go down towards the floor, leaving cold, stagnant, dry air in the lower regions of the room. This is an avoidable waste of energy.

According to another embodiment, a system 400A for routing disinfected airflow within a confined space, such as, a room is illustrated in FIG. 4A. The process involves routing the air coming out of the evaporator coil, furnace, blower or some similar components in an attic-based air-conditioning system through an embodiment of the apparatus for disinfecting air-conditioned airflow 100 (as described herein with reference to FIGS. 1A-1I). The airflow is subjected to disinfection in the apparatus 110 to kill and disable substantially all the microorganisms. The disinfected air can be routed into the room at the ground level using an air duct 410. A first end of the air duct 410 can be connected to an apparatus 110 while a second end of air duct 410 is located proximal to a ground level of the room. The air duct 410 can be configured to release the disinfected air through one or more supply vents which are positioned at substantially the ground level. The supplied air will travel the entire height of the room before it is routed through one or more return vents located at or near the ceiling. When the air traverses from the ground level to the return vents, air circulation is improved, and it also helps to heat the lower part of the room faster and more efficiently. The air moving up towards the return vents further carry the microorganisms from the room which are then be treated by apparatus 110, before it is again recirculated into the confined space through the supply vent. By locating a supply vent at the floor level and the return vent in the ceiling, an "auto-cleaning" of the recirculated air is facilitated. In the hot regions of the world, the inflow of air at the ground level brings much-needed cool air directly to the lower regions of the room with full force.

The supply duct 410 can be rigid, flexible, and configured to fit the space between the struts for manufacturing convenience. In one or more embodiments, a secondary supply duct 420 can be configured to route disinfected air at the ceiling while duct 410 can be configured to route air to the ground level. This process improves the cooling/heating of the confined space but it can also transport and destroy microorganisms settled on the floor of the confined space.

Figure 4B:
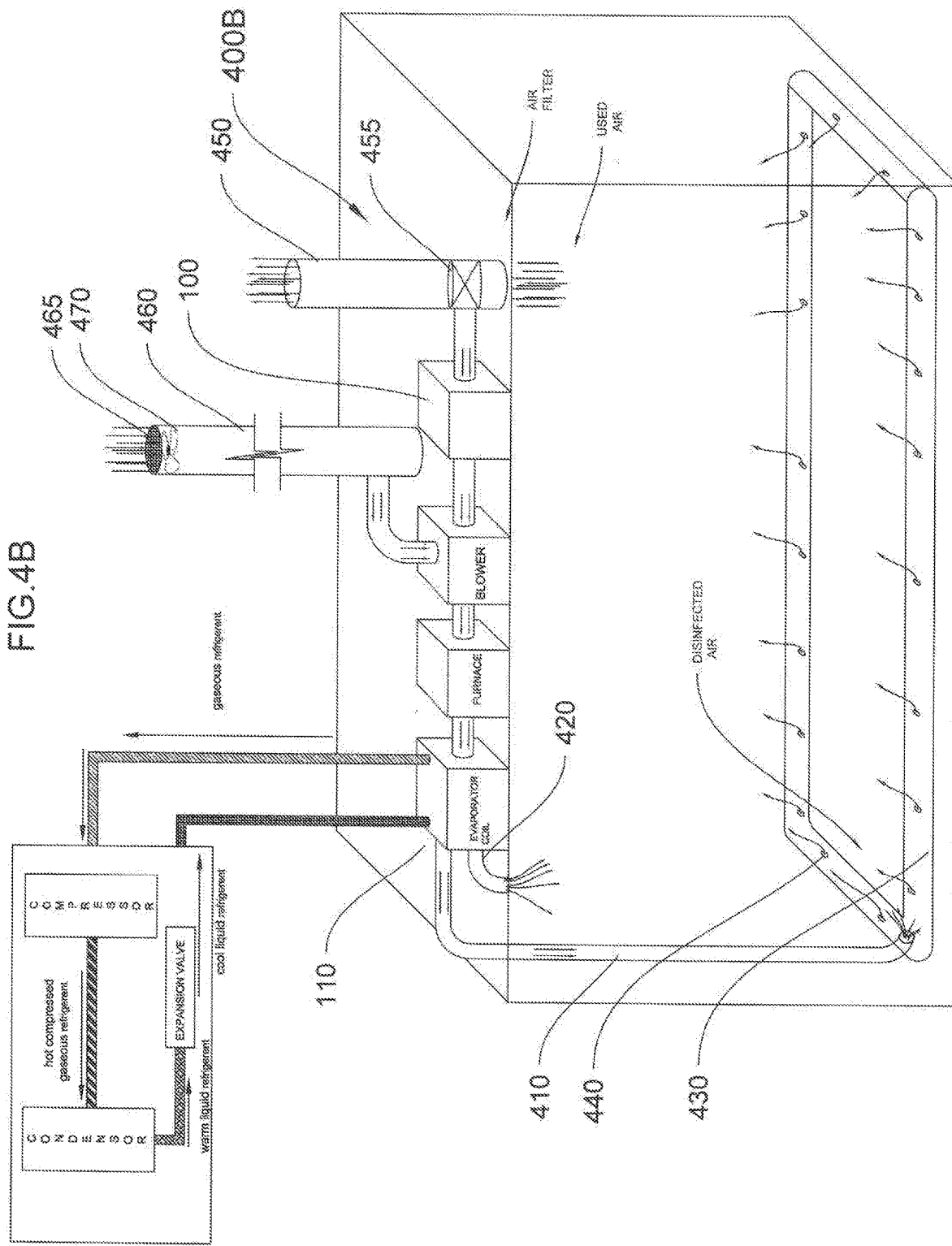
FIG. 4B illustrates a system for routing disinfected air to the floor of a confined space according to another embodiment.

According to another embodiment, a system 400B for routing disinfected airflow within a confined space, such as, a room is illustrated in FIG. 4B. As shown, the system 400B is used to deliver fresh, atmospheric air or disinfected recirculated air to a confined space. The system 400B comprises supply piping means 460 for routing "fresh" air from the atmosphere to a blower, furnace, evaporator coils, and other components of an air conditioning system. The supply piping 460 can include a HEPA filter 465 for filtering atmospheric air. One or more fans 470 can be provided proximal to the filter 465 to suck air into the supply piping 460. As described with reference to FIG. 4A, this airflow is supplied through duct 410 to the ground level of the confined space (and to the ceiling of the confined space through duct 420). A second end of duct 410 is coupled to duct 430. Duct 430 is positioned around the length and width/perimeter of the floor of the confined space. The duct 430 includes a plurality of vents/openings 440 for supplying air to the confined space. Since the air is supplied at the ground level, it will have to circulated through the confined space and travel the entire height of the confined space before it is routed through one or more return vents located at or near the ceiling.

The system 400 further comprises return piping means 450 for routing this circulated airflow. The piping 450 includes a bi-directional valve 455. The valve 455 can be configured to be opened such that at least a portion of the returned airflow is vented to the atmosphere. Alternately, the valve 455 can be completely opened such that the entire returned airflow is vented to the atmosphere, creating "totally fresh air conditioning" The opening and closing of valve 455 can be controlled by a programmable logic controller (not shown) known in the art.

When only a portion of the returned airflow is vented to the atmosphere, the remaining portion of the returned airflow is transported to an embodiment of an apparatus for disinfecting air-conditioned airflow 100 (as described herein with reference to FIGS. 1A-1I). The bi-directional valve 455 can be opened such that the portion of the returned airflow is routed to the apparatus 100. The airflow is subjected to disinfection in the apparatus 100 to kill and disable substantially all the microorganisms. The disinfected air can be supplied to the confined space using an air duct 410 (or a secondary supply duct 420). Air duct 410 is coupled to duct 430. Duct 430 has a plurality of vents/openings 440 for supplying the disinfected air to the confined space. As described earlier, this airflow traverses the height of the confined space before it is vented out through one or more return vents located in the ceiling. This process improves the cooling/heating of the confined space, but it can also transport and destroy microorganisms settled on the floor of the confined space.

Figure 4C:
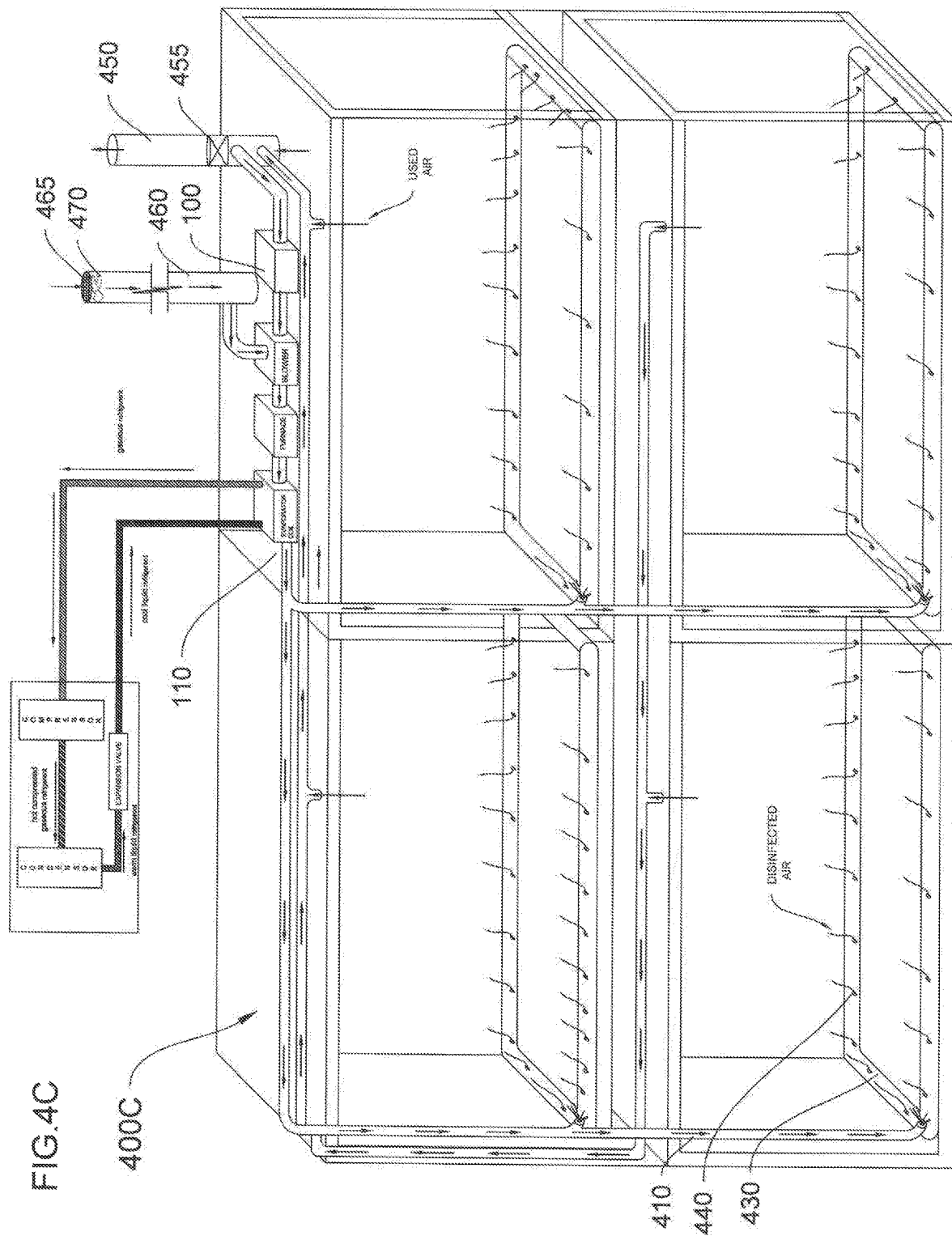
FIG. 4C illustrates a system for routing disinfected air to the floors of multiple confined spaces according to an embodiment.

FIG. 4C illustrates another embodiment 400C of the system described with reference to FIG. 4B. As shown, the system 400C is used to supply fresh, atmospheric air or disinfected recirculated air using duct 410 to a plurality of confined spaces (for example a building with multiple levels/stories and rooms). The supplied air can be provided at the floor level of each of the rooms/confined spaces using duct 430. The supplied air in each of the confined spaces is returned to the ceiling using return ducts 412 positioned along their respective ceilings. The process involves the steps described with reference to FIG. 4B and is not repeated for brevity.

Figure 5A:
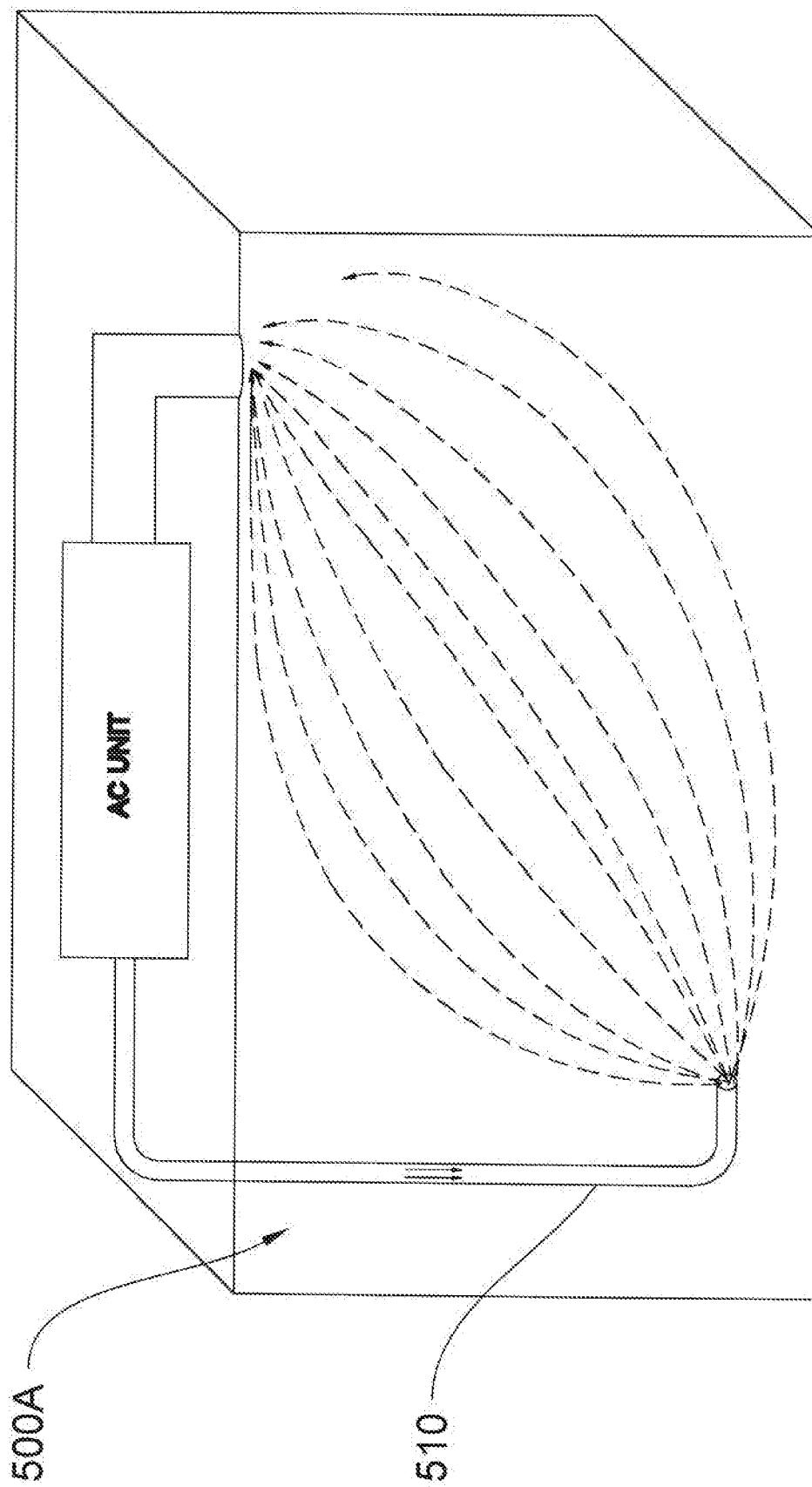
FIG. 5A illustrates a system for routing air-conditioned airflow to the floor of a confined space according to an embodiment.

In another embodiment, as shown in FIG. 5A, a system 500A for delivering air conditioned airflow is illustrated. The system involves a conventional attic-based split air conditioning system. A first end of air duct 510 is fluidly connected to a conventional air conditioning system. A second end of air duct 510 is connected to an air supply vent which is located at or near a ground level of a confined space. The supply vent releases heat/cooled airflow at substantially the ground level. The supplied air is required to travel the entire height of the room before it is routed through a return vent located at or near the ceiling. Therefore, by incorporating a duct 510, air from the attic can be routed to the ground level through the inside of the wall.

This process improves the cooling/heating of the confined space but it can also transport microorganisms settled in the floor to the return vent where it can be filtered by a conventional HEPA filter (not shown) connected to the air conditioning system, followed by the UV chamber to destroy/kill the remaining organisms.

In yet another embodiment, as shown in FIG. 5B, a system 500B for delivering air-conditioned airflow is illustrated. The system involves a conventional attic-based split air conditioning system. A first end of air duct 510 is fluidly connected to a conventional air-conditioning system. A second end of air duct 510 is connected to duct 520. Duct 520 is configured to extend around the perimeter of the floor confined space (similar to duct 430 shown in FIG. 4B). Duct 520 includes a plurality of openings/vents 530. The air conditioned air is supplied through vents 530 which are located at or near a ground level of a confined space. The supply vents 530 release heat/cooled airflow at substantially the ground level. The supplied air is required to travel the entire height of the room before it is routed through a return vent located at or near the ceiling. Therefore, by incorporating a duct 510, air from the attic can be routed to the ground level through the inside of the wall. This process improves the cooling/heating of the confined space but it can also transport microorganisms settled in the floor to the return vent where it can be filtered by a conventional HEPA filter (not shown) connected to the air conditioning system, followed by the UV chamber to destroy/kill the remaining organisms.

Figure 6:
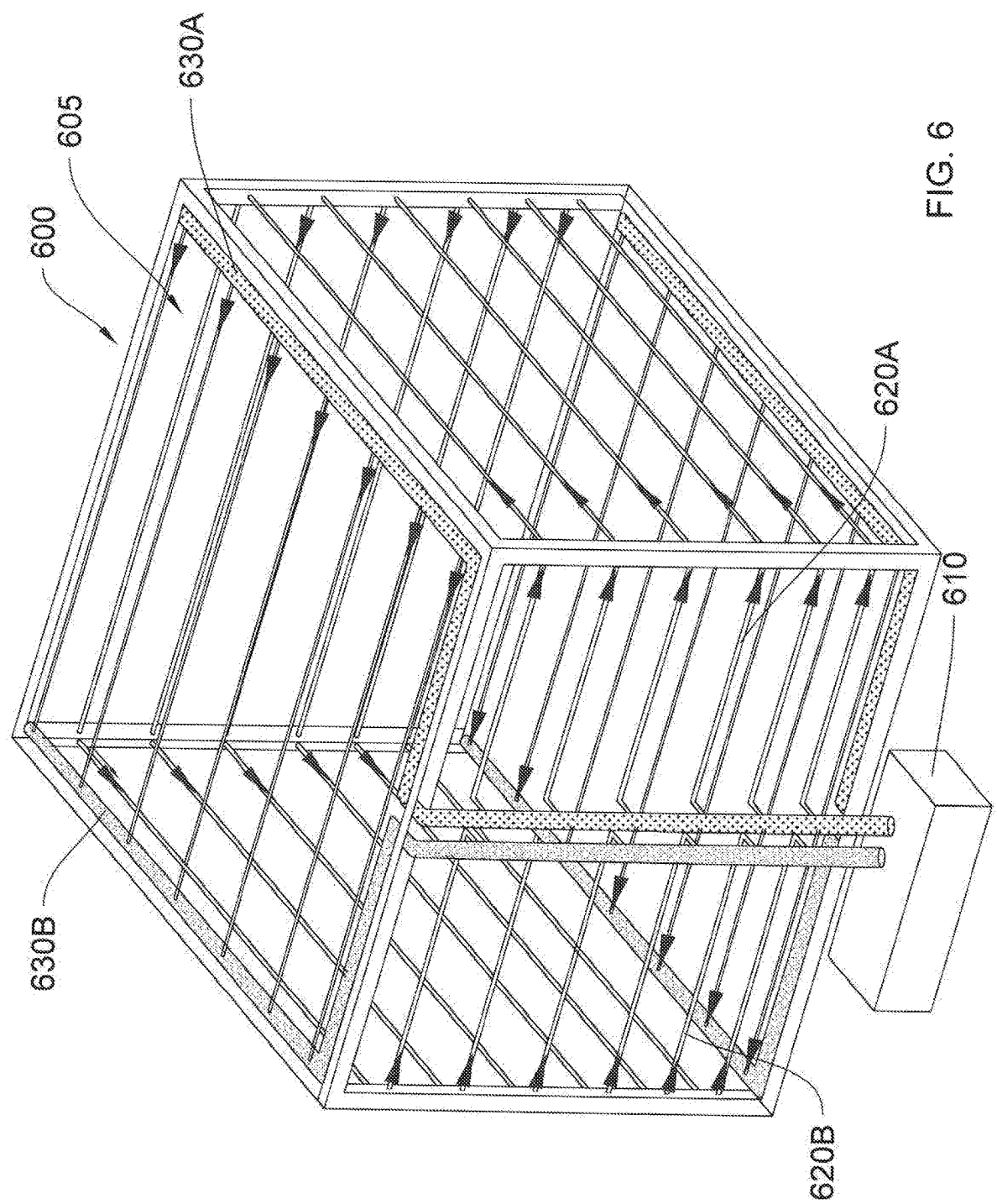
FIG. 6 illustrates a system for heating and cooling a confined space according to an embodiment, without using air condition.
Figure 9A:
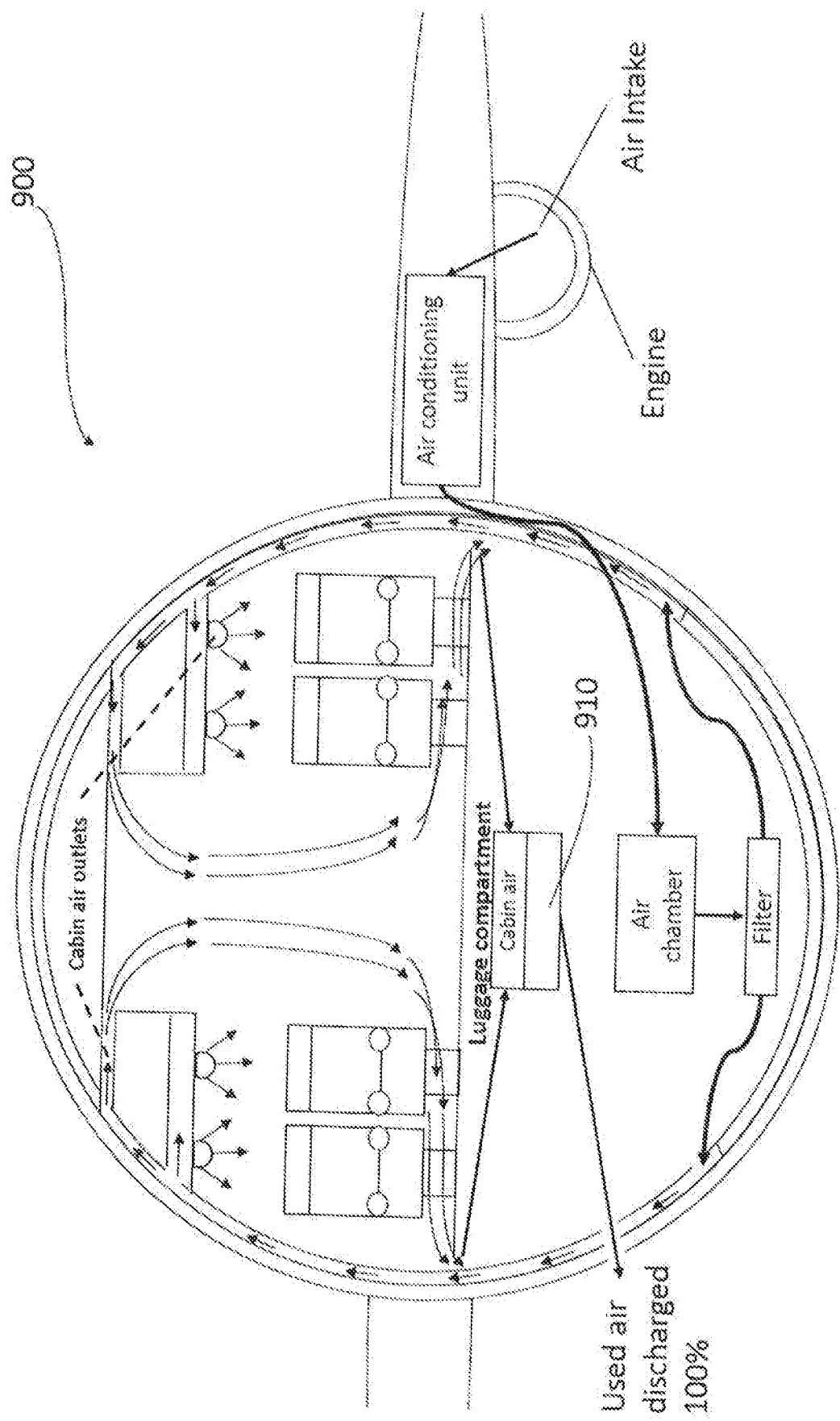
FIGS. 9A-9B illustrate a system for discarding used/contaminated cabin air outside an airplane according to an embodiment.
Figure 9B:
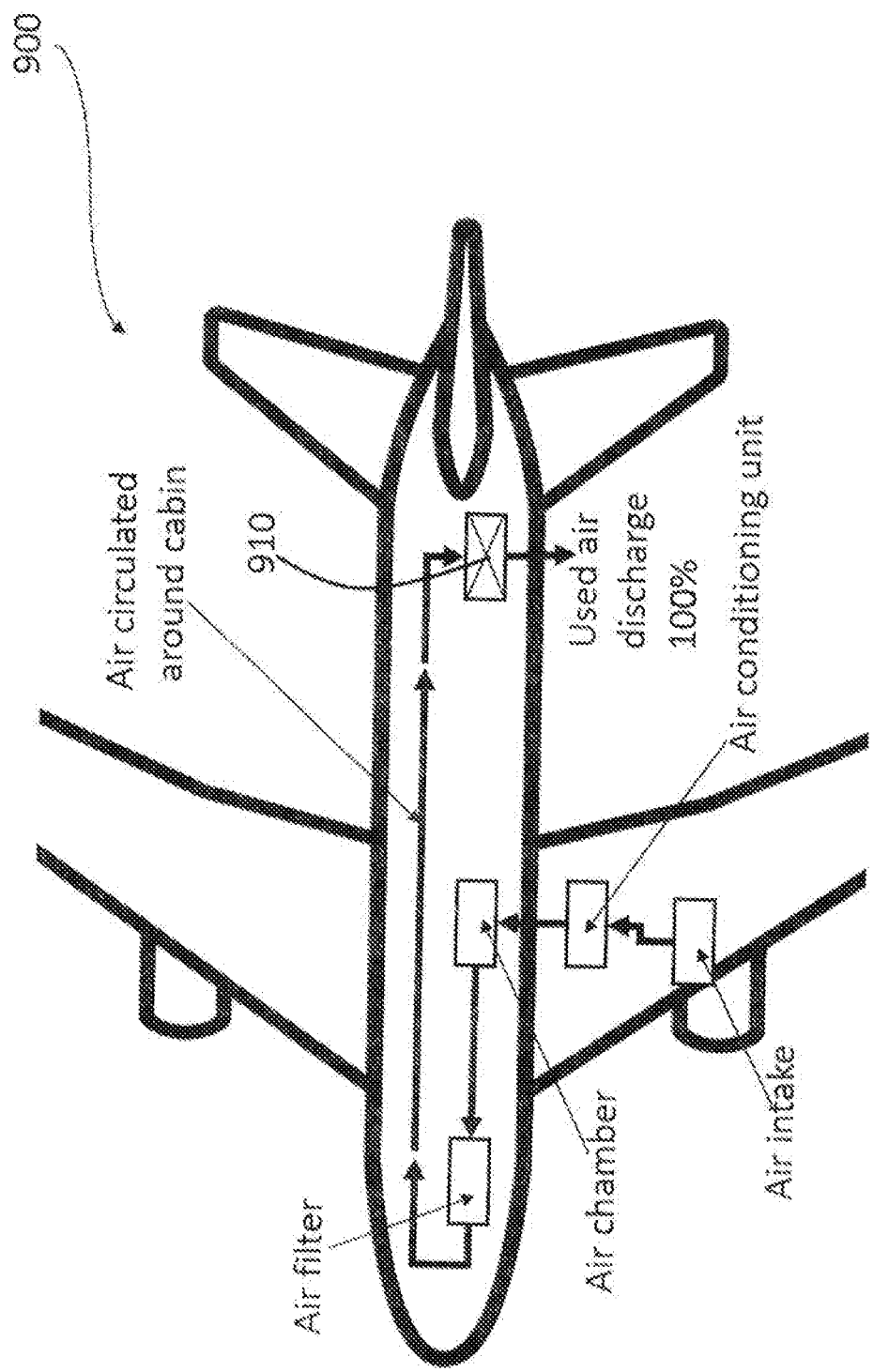
Figure 9C:
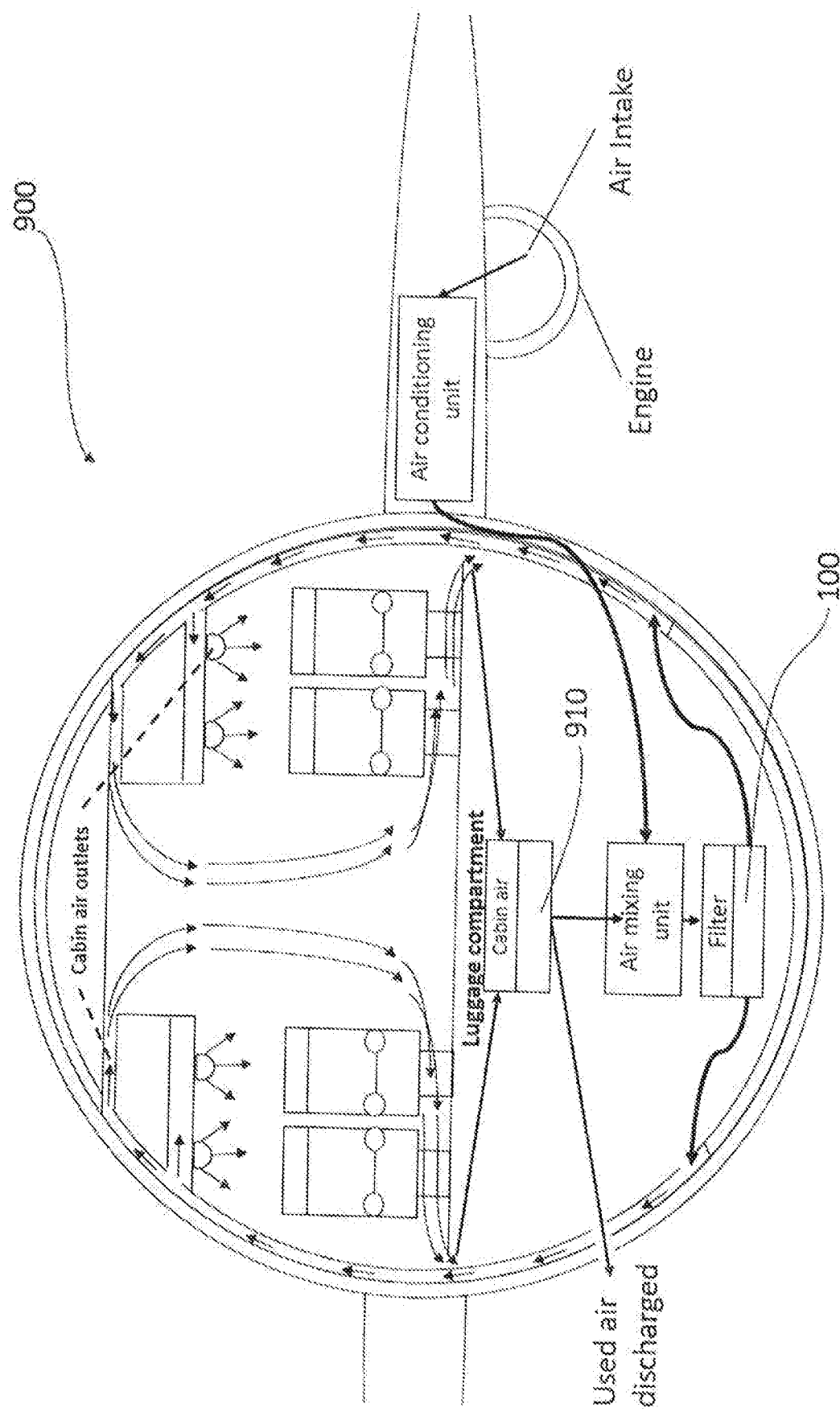
FIGS. 9C-9D illustrate a system for disinfecting the air so that the cabin air can be recirculated according to an embodiment.
Figure 9D:
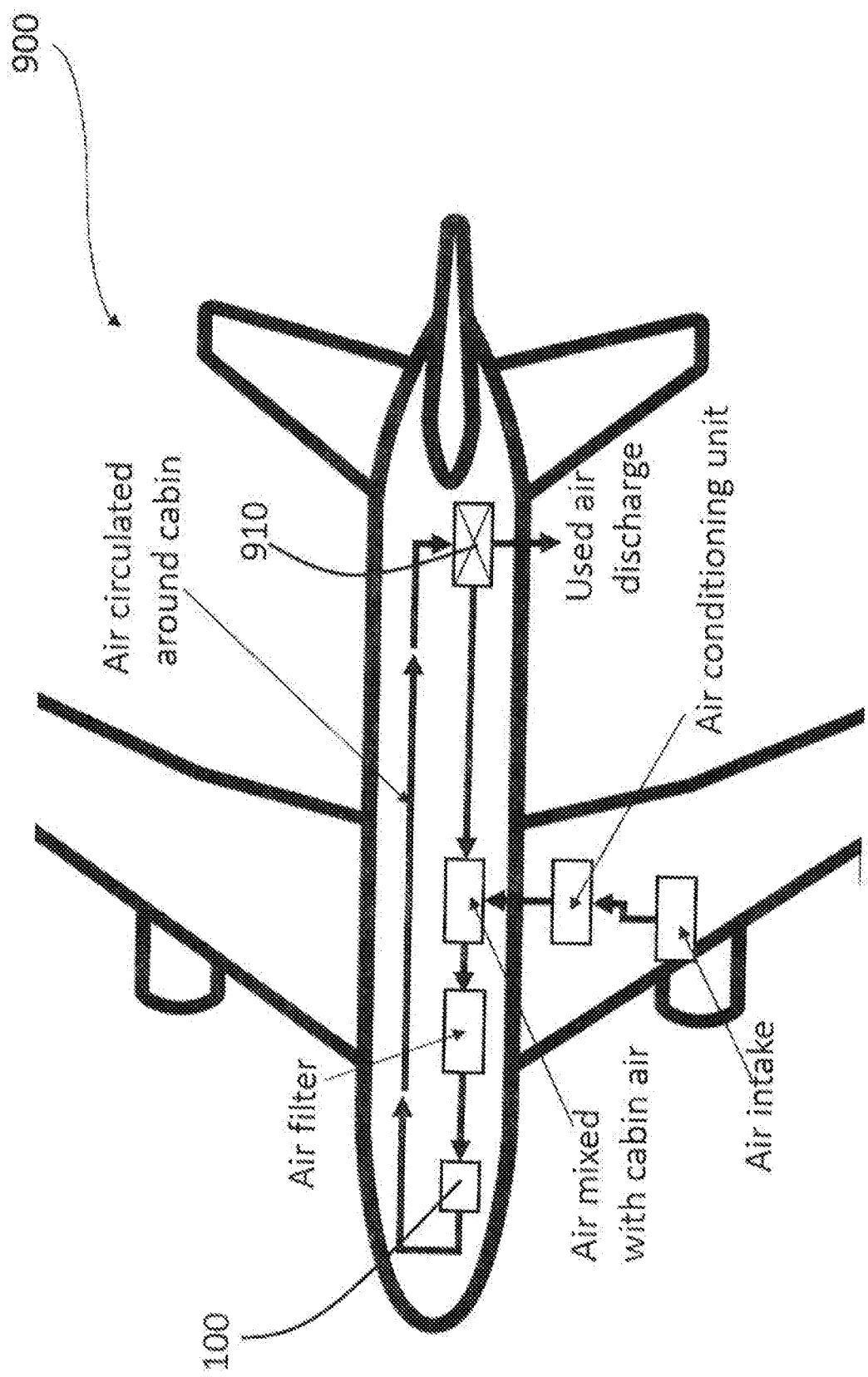
Figure 9E:
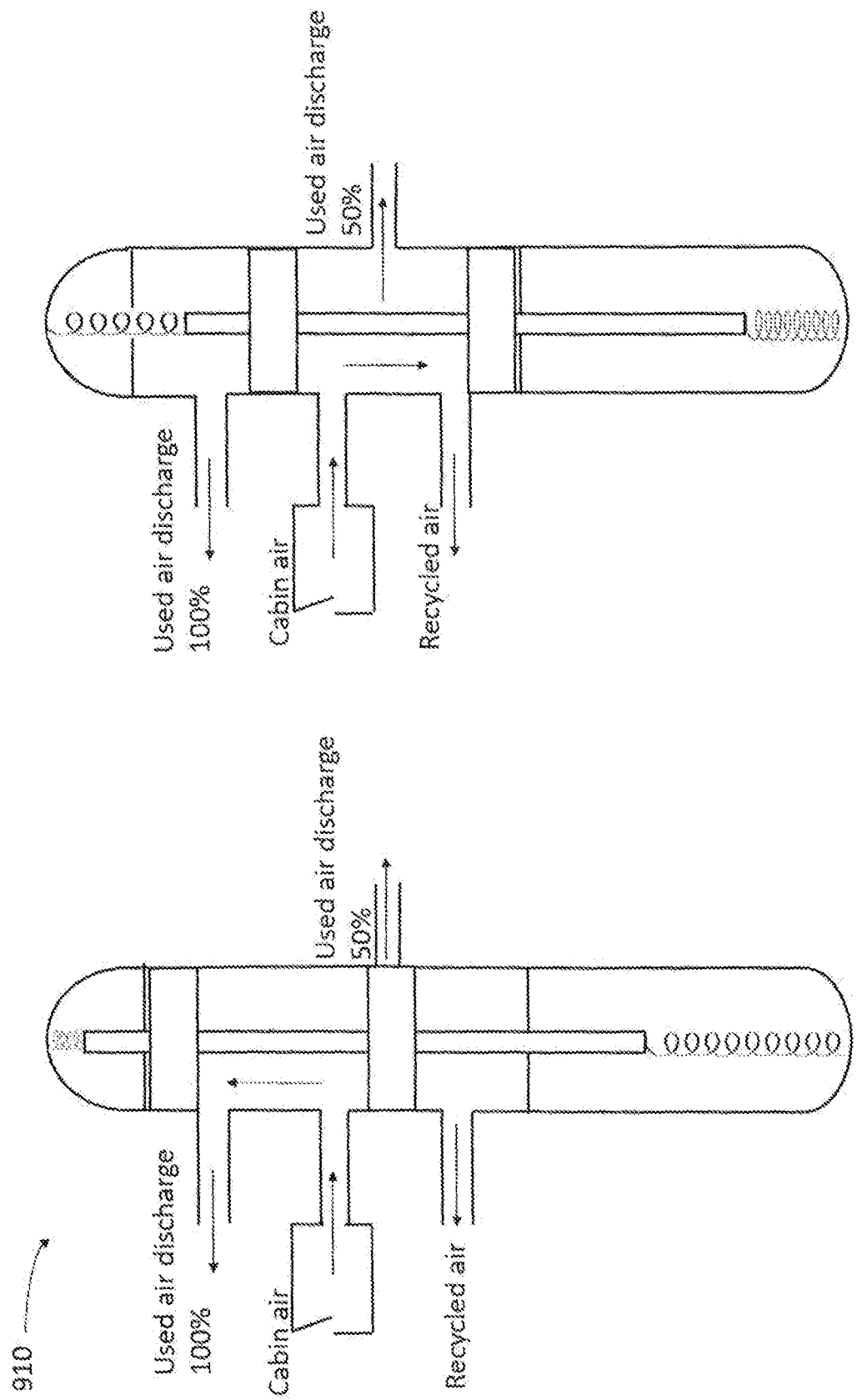
FIG. 9E illustrates a bi-directional valve for routing airflow into or outside an airplane according to an embodiment.

In yet another embodiment, as shown in FIG. 6, a system 600 for heating and cooling a confined space/room 605 without using an air-conditioning system is disclosed. The system involves overlaying, on sheetrock, piping means for transporting hot and/or cold water along the sidewalls, base and ceiling of the room 605. The piping means are connected to a programmable logic controller 610, with an incorporated pump, which can be used to adjust the temperature of the water, and pump it out. The piping means can include a plurality of small diameter tubes 620 with running water. The small diameter tubes 620 are overlaid on the sidewalls of the room, floor and ceiling. This system 600 can be utilized for verifying the beneficial aspects of supplying air at the ground level. The inventor has postulated that these beneficial aspects can be determined only in a confined room with preset temperature without the benefit of an air conditioned airflow. This is accomplished by circulating hot/cold water through fine tubes 620 overlaid on the sheetrock (not shown) inside the room 605. The water needs to be treated with saline or other chemical compounds to create extreme (cold/hot) temperatures. Water is heated or cooled to a desired temperature by the programmable logic controller 610 and is circulated through outgoing large tubes 630A. The fine tubes 620A carry the water out and then relayed to fine tubes 620B. The large return tubes 630B collect water from fine tubes 620B from where it is returned it to the programmable logic controller 610 where the lost temperature is replenished and pumped again through 630A. In a confined room as shown, the effect of air coming from the ceiling and that coming from the ground level can be compared to modify the temperature and air current in the lower part of the room where people move around. It can also be used to compare the virus count at the ground level with a conventional air conditioning system as compared with the systems illustrated in FIGS. 5A and 5B. Temperature control of the room with air conditioning will not allow this critical evaluation.

FIGS. 8A-8B illustrate air conditioned airflow in an aircraft, such as, a commercial airplane. Outside/atmospheric air enters the airplane through the engine turbines, where it is compressed, the air passes through cooling/heating packs located beneath the cabin. These packs regulate the temperature of the compressed air. The air is then passed through an air mixing unit, filtered through a HEPA filter and circulated back into the cabin. Air from the cabin also travels to the air mixing unit. The mixed air enters the cabin through overhead vents and moves downward in a circular motion. A portion of this air is recirculated, while most of it leaves the cabin through floor vents. Almost half of the cabin air is dumped outside, while the rest is sent back to HEPA filters to mix again with the fresh outside air.

According to another embodiment, a system 900 for discarding used/contaminated air in an airplane is shown in FIGS. 9A and 9B. FIGS. 9C-9D illustrate a system 900 for disinfecting the air so that the cabin air can be recirculated according to an embodiment. FIG. 9E illustrates a bi-directional valve for routing airflow into or outside an airplane according to an embodiment.

Currently, atmospheric/outside air continually enters the airplane through its engine turbines. The air is compressed which causes it to be heated. It then passes through cooling packs which are located below the cabin. The cooling packs regulate the temperature of the compressed air. The cooled air is infused through an air mixing unit and circulated into the cabin. Simultaneously, air from the cabin ("used air") passes through HEPA filters and is infused through the air mixing unit. The mixture of used air and fresh outside air enters the cabin through overhead vents. A portion of this air is recirculated while the remaining leaves the cabin through floor vents. In order to maintain cabin pressure, typically, only about half of the exited cabin air is dumped outside the airplane while the rest is sent back to HEPA filters and mixed with the fresh outside air before it is recirculated into the cabin.

As shown, outside air is cooled/heated and passed through an air mixing unit where it mixes with cabin air. This air is then passed through a HEPA filter and then through an apparatus 100 (as disclosed herein with reference to FIGS. 1A-1H) which is in fluid communication with the air mixing unit. The apparatus 100 includes a disinfection chamber comprising a plurality of UV light sources which can emit germicidal far UV-C light. The air received from the air mixing unit is disinfected inside the apparatus 100 and delivered to the cabin.

The air inside an airplane is purified either by: (i) disinfecting recirculated cabin air within the apparatus for disinfecting air disclosed herein, or (ii) entirely avoiding the recirculation of used cabin air. The air purification process involves connecting a bi-directional valve 910 to an airplane's air mixing unit. When the bi-directional valve 910 is in an open position, the contaminated/used cabin air is continually discarded outside the airplane while fresh air is continually drawn in to the airplane though its engine turbines. Under these conditions, recirculation of used cabin air is completely avoided and the air entering the cabin is totally fresh atmospheric air.

As shown in FIG. 9E, the bi-directional valve 910 can be set to one of an open/close/partially open state. Typically, the bi-directional valve 910 is set to a "fully opened" state if the airplane does not include the apparatus 100. This ensures that used cabin air is continually dumped outside. The bi-directional valve 910 can be set to a partially or fully closed state if the airplane is provided with the apparatus 100. The bi-directional valve 910 can also be provided with a mechanism for maintaining the cabin pressure when used air is discarded or sent back to the air mixing unit. The bi-directional valve includes a door/opening that opens only after the cabin pressure is maintained at a pre-determined desired level. As mentioned earlier, when the bi-directional valve 910 is opened completely, the contaminated/used cabin air is totally discarded, while maintaining the cabin pressure at a desired level. Since fresh air is continually drawn in through the turbines, the air in the cabin is 100% fresh air. The fresh air is heated/cooled, as described earlier, filtered by the HEPA filters, and sent to the cabin. Alternately, the cabin air can be treated with the apparatus for disinfecting air 100, as disclosed herein. In this embodiment, the bi-directional valve 910 is closed. Used cabin air is filtered with a HEPA filter and routed to the apparatus 100. The apparatus 100 is configured to destroy the microorganisms that are not filtered by the HEPA filter. The filtered, disinfected mixture of fresh air and the used cabin air can now be safely sent back to the cabin. In certain embodiments, a measured amount of used cabin air can be released by leaving the bi-directional valve in at least a partially open state. By partially opening the bi-directional valve, the load on the apparatus 100 can be reduced.

Therefore, the present invention is well suited to destroy airborne pathogens in confined spaces having recirculating air. For example, it can be used to contain the spread of SARS-CoV-2 virus (or similar viruses) in confined spaces. It can also be used to contain the spread of bacteria that cause Legionnaires' disease.

While the systems and methods of disinfecting recirculated air are described in terms of "comprising," "containing," or "including" various components or steps, the system and methods also can "consist essentially of" or "consist of" the various components and steps. Each of the appended claims defines a separate invention, which for infringement purposes is recognized as including equivalents to the various elements or limitations specified in the claims. Depending on the context, all references herein to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

The invention claimed is:

1. An apparatus for disinfecting air-conditioned airflow in a confined space, comprising:
   a modular housing, the housing positioned inline with an air conditioning system, the housing comprising:
   (i) an outer cylinder; and
   (ii) a solid cylindrical rod member positioned within the outer cylinder, wherein
   the cylindrical rod member extends the length of the outer cylinder;
   a disinfection chamber enclosed within the housing, wherein the disinfection chamber comprises a plurality of disinfection sheets, wherein each disinfection sheet comprises a plurality of tubular ultraviolet (UV) light sources, wherein the UV light sources are configured to extend substantially the length of the solid cylindrical rod member, wherein a first disinfection sheet is disposed around an inner circumference of the outer cylinder, and wherein a second disinfection sheet is disposed around an outer circumference of the cylindrical rod member; and
   a substantially spiral or helical airflow diverter positioned in an annular passage formed between the first disinfection sheet and the second disinfection sheet, wherein the airflow diverter creates a serpentine pathway for airflow within the housing to expose microorganisms in the airflow within the housing to UV-C or far UV-C light emitted by the UV light sources for an extended and optimal duration,
   wherein the apparatus is configured to eliminate SARS-CoV-2 in the airflow.

2. The apparatus according to claim 1, each disinfection sheet further comprises a plurality of removable connectors, and wherein a UV light source in a disinfection sheet is connected to an adjacent UV light source by a transparent connector.

3. The apparatus according to claim 1, wherein the distance between each spiral turn of the airflow diverter is configured to be increased or decreased to increase or slow the passage of the airflow to be disinfected.

4. The apparatus according to claim 1, wherein the airflow diverter is further configured to force the airflow to travel over the first and second disinfection sheets.

5. The apparatus according to claim 1, wherein the tubular UV light sources are arranged along a longitudinal axis of the first disinfection sheet and the second disinfection sheet.

6. The apparatus according to claim 5, wherein the apparatus is configured to provide a continual supply of disinfected air.

7. A process for disinfecting a recirculated airflow in a confined space, comprising:
   providing an apparatus for disinfecting an air-conditioned airflow according to claim 1, wherein the apparatus is fluidly connected to a conventional HVAC system, and wherein the airflow is treated with germicidal UV-C/far UV-C light inside the apparatus;
   supplying a stream of disinfected heated/cooled air to the confined space through a supply vent located at or near a floor of the confined space; and
   routing used air from the confined space through a return vent positioned at or near a ceiling of the confined space.

8. The process according to claim 7, wherein the supply vent is connected to a secondary air duct, wherein the secondary air duct is arranged along a perimeter of the floor, and wherein the secondary air duct comprises a plurality of secondary vents for supplying the heated/cooled air.

9. The process according to claim 8, wherein the return vent comprises a bi-directional valve for routing at least a portion of the used air back to the apparatus for disinfection.

10. The process according to claim 7, wherein the return vent is configured to route substantially all the used air to the atmosphere.

11. An apparatus for disinfecting air-conditioned airflow in a confined space, comprising:
- a modular housing, the housing positioned inline with an air conditioning system, the housing comprising:
  - (i) an outer cylinder; and
  - (ii) a solid cylindrical rod member positioned within the outer cylinder, wherein the cylindrical rod member extends the length of the outer cylinder;
- a disinfection chamber enclosed within the housing, wherein the disinfection chamber comprises a plurality of disinfection sheets, wherein each disinfection sheet comprises a plurality of tubular ultraviolet (UV) light sources, wherein the UV light sources are configured to extend substantially the length of the solid cylindrical rod member, wherein a first disinfection sheet is disposed around an inner circumference of the outer cylinder, and wherein a second disinfection sheet is disposed around an outer circumference of the cylindrical rod member; and
- a substantially spiral or helical airflow diverter positioned in an annular passage formed between the first disinfection sheet and the second disinfection sheet, wherein the airflow diverter creates a serpentine pathway for airflow within the housing to expose microorganisms in the airflow within the housing to UV-C or far UV-C light emitted by the UV light sources for an extended and optimal duration, the airflow diverter is further configured to force the airflow to travel over the first and second disinfection sheets.

12. The apparatus according to claim 11, wherein the apparatus is configured to eliminate SARS-CoV-2 in the airflow.

\* \* \* \* \*